(12) United States Patent
Parish et al.

(10) Patent No.: US 10,874,383 B2
(45) Date of Patent: Dec. 29, 2020

(54) ADHESIVE APPLICATOR

(71) Applicant: ADVANCED MEDICAL SOLUTIONS LIMITED, Winsford (GB)

(72) Inventors: Simon Mark Parish, Exeter (GB); Nithinkrishnan Gopalakrishnan, Plymouth (GB); Guy Stephen Miller, Cornwall (GB)

(73) Assignee: ADVANCED MEDICAL SOLUTIONS LIMITED, Cheshire (GB)

(*) Notice: Subject to any disclaimer, the term of this patent is extended or adjusted under 35 U.S.C. 154(b) by 0 days.

(21) Appl. No.: 16/474,756

(22) PCT Filed: Dec. 22, 2017

(86) PCT No.: PCT/GB2017/053889
§ 371 (c)(1),
(2) Date: Jun. 28, 2019

(87) PCT Pub. No.: WO2018/122554
PCT Pub. Date: Jul. 5, 2018

(65) Prior Publication Data
US 2019/0343502 A1    Nov. 14, 2019

(30) Foreign Application Priority Data
Dec. 30, 2016 (GB) .................... 1622423.0

(51) Int. Cl.
*A61B 17/00* (2006.01)
*B05C 17/01* (2006.01)
(Continued)

(52) U.S. Cl.
CPC .... *A61B 17/00491* (2013.01); *B05C 17/0116* (2013.01); *A61B 2090/035* (2016.02); *A61B 2090/0807* (2016.02); *A61M 5/204* (2013.01)

(58) Field of Classification Search
CPC ........ A61B 17/00491; A61B 2090/035; A61B 2090/0807; A61B 2017/00535; B05C 17/0116; A61M 5/204
See application file for complete search history.

(56) References Cited

U.S. PATENT DOCUMENTS 3,353,537 A    11/1967   Knox et al.
3,727,614 A *   4/1973   Kniazuk ............... A61M 5/204
                                                  604/115
(Continued)

FOREIGN PATENT DOCUMENTS

FR      761652         3/1934
WO      2010/145041    12/2010
WO      2014/072688    5/2014

OTHER PUBLICATIONS

International Search Report for PCT/GB2017/053889, dated Mar. 5, 2018, 3 pages.
IPRP for PCT/GB2017/053889, dated Jul. 2, 2019. (6 pages).

*Primary Examiner* — Frederick C Nicolas
(74) *Attorney, Agent, or Firm* — Nixon & Vanderhye P.C.

(57) ABSTRACT

An applicator for dispensing a liquid, the applicator including: a body, a holder for holding a supply of liquid to be dispensed, a nozzle mounted on the body for dispensing the liquid, an elongate priming chamber within the body for receiving liquid from the holder, an elongate delivery chamber within the body for receiving liquid from the priming chamber, a piston assembly having a piston located in the delivery chamber and being moveable in a first direction to draw liquid from the priming chamber into the delivery chamber and in a second opposite direction for passing (Continued)

liquid from the delivery chamber to the nozzle, a drive arrangement capable of effecting incremental movement of the piston in the second direction for metered dispense of the liquid, and a first actuator for operating the drive arrangement for effecting the incremental movement.

23 Claims, 16 Drawing Sheets

(51) Int. Cl.
*A61B 90/00* (2016.01)
*A61M 5/20* (2006.01)

(56) References Cited

U.S. PATENT DOCUMENTS

| | | | |
|---|---|---|---|
| 3,758,005 A * | 9/1973 | Christine | B05C 17/00569 222/309 |
| 4,103,684 A * | 8/1978 | Ismach | A61M 5/30 604/71 |
| 4,643,723 A * | 2/1987 | Smit | A61M 5/204 604/207 |
| 5,456,388 A * | 10/1995 | Honstein | A61M 5/31525 222/390 |
| 5,833,661 A * | 11/1998 | Trapp | A61M 5/20 604/147 |
| 5,843,042 A | 12/1998 | Ren | |
| 2014/0079686 A1 | 3/2014 | Barman et al. | |

\* cited by examiner

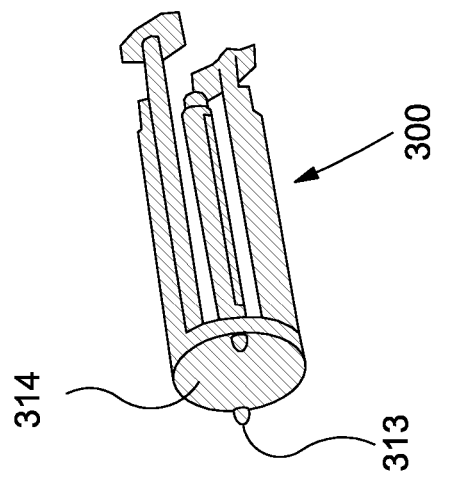
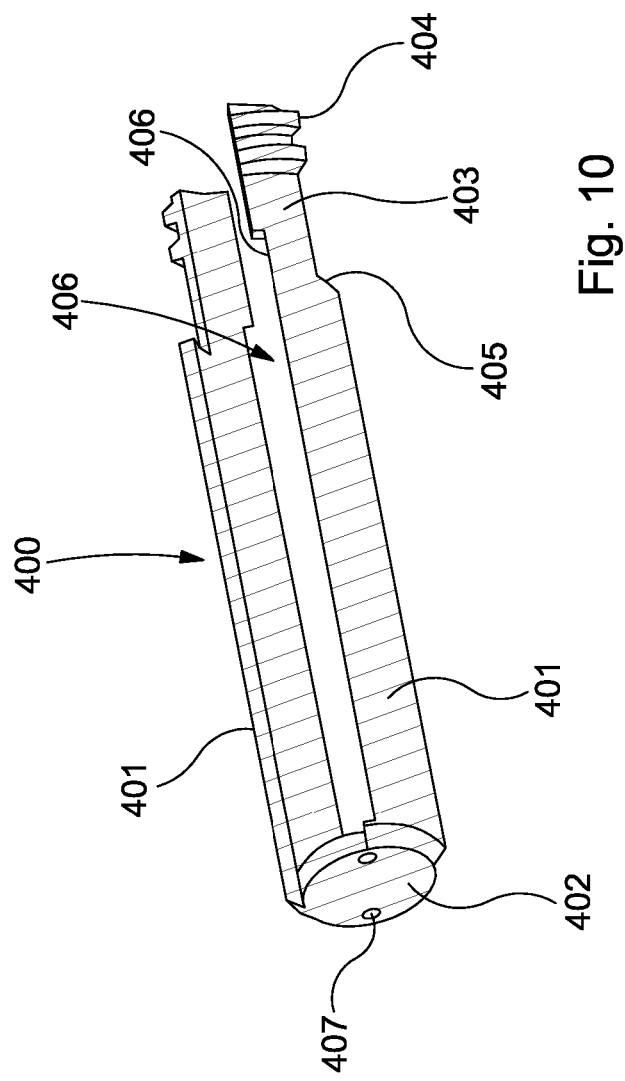
Fig. 10

ADHESIVE APPLICATOR

This application is the U.S. national phase of International Application No. PCT/GB2017/053889 filed 22 Dec. 2017, which designated the U.S. and claims priority to GB Patent Application No. 1622423.0 filed 30 Dec. 2016, the entire contents of each of which are hereby incorporated by reference.

BACKGROUND & BRIEF SUMMARY

The present invention relates to an applicator for dispensing a liquid. The invention relates particularly, but by no means exclusively, to such an applicator in the form of a surgical implement for dispensing a medical adhesive (e.g. a coolable cyanoacrylate adhesive) to a site in patient's body during a surgical procedure.

According to the present invention there is provided an applicator for dispensing a liquid, the applicator comprising;
- a body,
- a holder for holding a supply of liquid to be dispensed,
- a nozzle mounted on the body for dispensing the liquid,
- an elongate priming chamber within the body for receiving liquid from the holder,
- an elongate delivery chamber within the body for receiving liquid from the priming chamber,
- a piston assembly having a piston located in the delivery chamber and being moveable in a first direction to draw liquid from the priming chamber into the delivery chamber and in a second opposite direction for passing liquid from the delivery chamber to the nozzle,
- a drive arrangement capable of effecting incremental movement of the piston in the second direction for metered dispense of the liquid, and
- a first actuator for operating the drive arrangement for effecting said incremental movement.

The applicator of the invention is particularly useful as a surgical instrument for the delivery of a curable, liquid adhesive formulation to a tissue site within a patient's body during a surgical procedure that also has application to topical administration of such adhesive to effect closure of skin wounds. Certain embodiments of the invention may have a dual function, for which purpose the applicator may have a first nozzle configured to apply adhesive in the form of droplets at an internal tissue site and a second nozzle, over which the first nozzle is removably mounted, revealed on removal of the first nozzle and configured to apply the liquid in the form of a stripe, e.g. for effecting skin closure.

In a preferred embodiment of the invention, the holder serves to hold a frangible ampule of the liquid to be dispensed and is associated with a breaker arrangement to fracture the ampule to allow the contents thereof to be passed to the priming chamber (for subsequent passage to the delivery chamber). The breaker arrangement may be one operated by rotary movement of the holder. Thus the holder may have internal cam surfaces arranged such that rotation of the holder results in a compressive force being applied transversely to the ampule to effect fracture thereof. Alternatively, the breaker arrangement may be one operated by linear movement of the holder, in which case the holder may have internal cam surfaces configured such that axial movement of the holder relative to the ampule results in a transverse compressive force being applied to the ampule to effect fracture thereof.

In preferred constructions of applicator in accordance with the invention, the primary and delivery chambers are coaxial with each other. Alternatively or additionally it is preferred that these priming and delivery chambers are relatively fixed within the body of the applicator and movement of the piston in the first direction (to cause liquid to be drawn into the delivery chamber) is effected by the holder being moved axially of the body to engage the piston new assembly and cause the piston to move in the first direction. Most preferably this movement of the piston is effected by a linear movement of the holder. The holder may, for example, have at least one projection (e.g. a finger or the like) which for the purposes of effecting movement of the piston assembly, engages at a free end thereof with the free end of an arm or the like of the piston assembly, whereby in movement of the holder pushes the piston assembly in the first direction. Preferably the linear movement of the holder is a guided movement, e.g. a pin (or pins) on the holder may engage with a track (or tracks) on the inside of the body of the applicator. Preferably also, there is a rotation of the holder relative to the piston assembly as the latter approaches the end of its movement in the first direction so that the reverse movement of the piston assembly (i.e. to move the piston in the second direction) is not hindered by the holder. This relative rotary movement may be effected by extending the linear guide track(s) to curve around the interior of the body of the applicator whereby the pin(s) in following the track(s) in part a rotary motion to the rotary holder.

Preferably also, movement of the piston assembly in the first direction (during which liquid is drawn into the priming chamber) is effected with the piston assembly disengaged from the drive arrangement. It is particularly preferred that the piston assembly is linearly movable in the first direction from a first position to a second position and is then rotationally movable (preferably about the axis of the piston) from a second position to a third position to allow for movement of the piston assembly in the second direction by operation of the drive arrangement. Movement of the piston assembly in accordance with this sequence may be controlled by virtue of a pin or pins on the piston assembly engaging in a guide track formation provided on the body and configured to provide the defined sequence of movement.

Preferably the piston assembly is movable in the second direction from an initial fourth position to a fifth position without operation of the drive arrangement and is movable from this fifth position to a sixth position by operation of the drive arrangement which effects the incremental movement of the piston. The applicator preferably comprises a carriage engageable by the piston assembly at its fourth position and being operable to effect movement of the piston assembly in the second direction from the fourth to the fifth position. This movement of the piston assembly from its fourth to fifth position allows for a short movement of the piston in the second direction to allow air to be purged from a conduit connecting the delivery chamber to the nozzle and for the conduit to be filled with adhesive in readiness for use of the device.

For the purpose of effecting movement of the carriage (for movement of the piston assembly from its fourth to fifth position) the applicator may comprise a second actuator rotatably mounted on the body of the applicator. This second actuator may have a screw thread formation operatively associated with a complementary screw thread formation provided on the carriage, whereby rotation of the actuator effects movement of the carriage in the second direction to move the piston assembly from its fourth to fifth position.

In preferred embodiments of the invention, the priming and delivery chambers are coaxial with each other and the applicator further comprises an intermediate chamber between adjacent ends of the priming and delivery chambers and coaxial therewith. A liquid outlet is connected to the intermediate chamber and there is an axially movable filter in the intermediate chamber. The axially movable filter is configured as a valve that is movable from a first position in which the liquid outlet is closed to liquid flow from the delivery chamber but the valve allows liquid to pass from the priming chamber to the delivery chamber, to a second position in which liquid can flow from the delivery chamber to the outlet but not between the priming chamber and the delivery chamber.

Having regard to the above considerations, a preferred applicator in accordance with the invention is one in which:

(i) a holder holding a frangible ampule of a liquid to be dispensed by the ampule is linearly movable in the grip of the body of the housing and configured to engage the piston assembly to push that assembly in the first direction and is subsequently rotatable to disengage from the piston assembly;

(ii) the piston assembly is movable in the first direction without engagement of the drive arrangement and is rotatable towards the end of its travel in the first direction to allow for movement in the second direction with engagement of the drive;

(iii) the piston assembly is movable in the second direction from an initial fourth position to a second position without operation of the drive arrangement and is movable from this fifth position to a sixth position by operation of the drive arrangement;

(iv) a carriage linearly movable by operation of a rotary (second) actuator on the body of the applicator is provided and serves to effect movement of the distant assembly from the fourth to the fifth position; and (v) a valve with a filter unit is provided between the priming and delivery chambers as described above.

In such a construction, there is preferably an interlock system which allows linear inward movement of the holder and its subsequent rotational movement (whilst preventing rotation of the second actuator) and then locks the holder against further rotational movement and allows rotation of the rotary actuator. In this way, the steps of transfer of the liquid to the priming chamber and subsequent filling of the conduit that extends from the transfer chamber to the nozzle with liquid can only be effected in the required order, thus eliminating possible user error.

BRIEF DESCRIPTION OF THE DRAWINGS

The invention will be further described, by way of example only, with reference to the accompanying drawings, in which:

FIG. 10 illustrates the priming carriage and piston assembly in the applicator;

DETAILED DESCRIPTION

Figure 1:
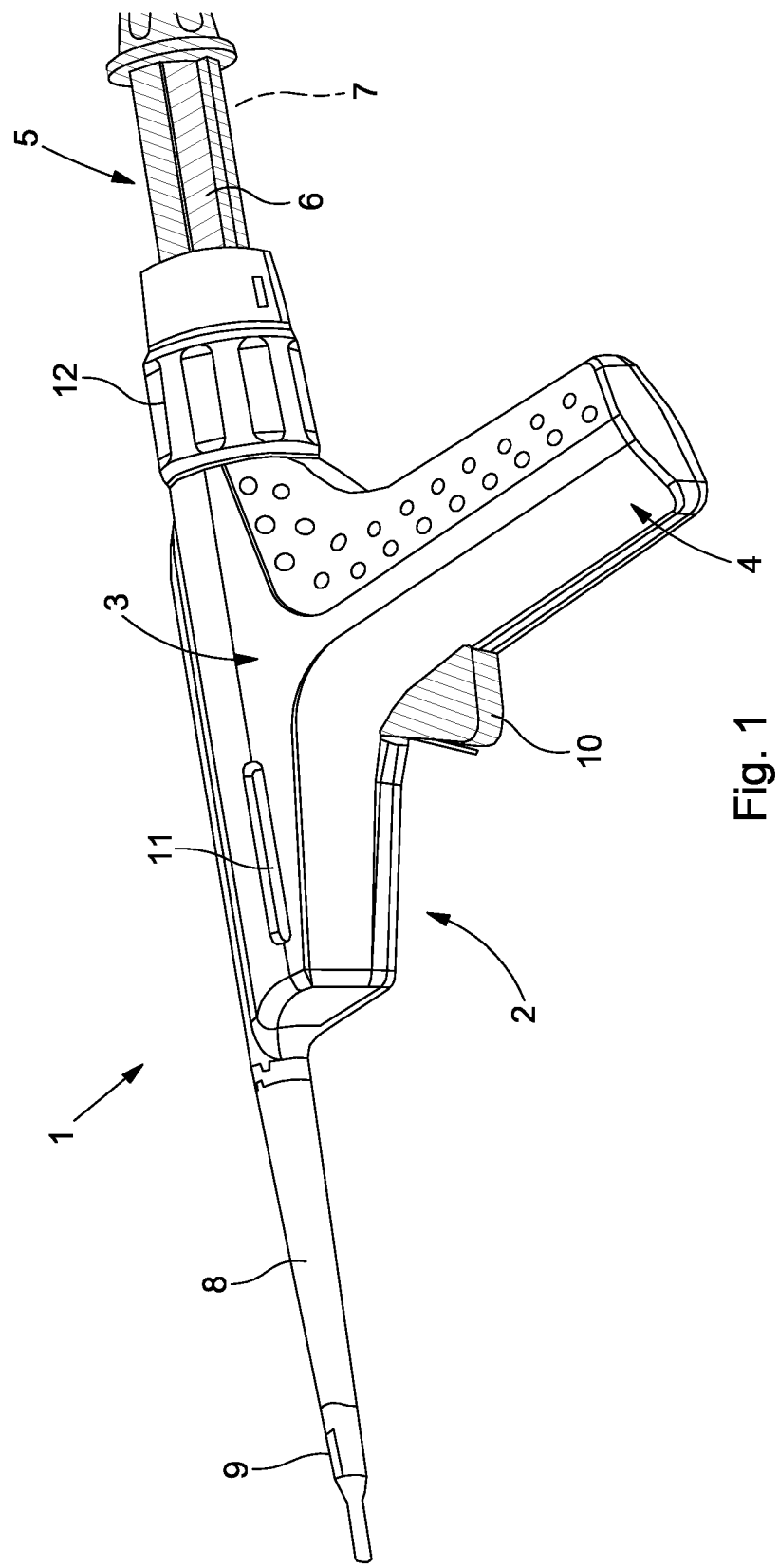
FIG. 1 is a side view of one embodiment of applicator 1 in accordance with the invention in the "as supplied" configuration.
Figure 2:
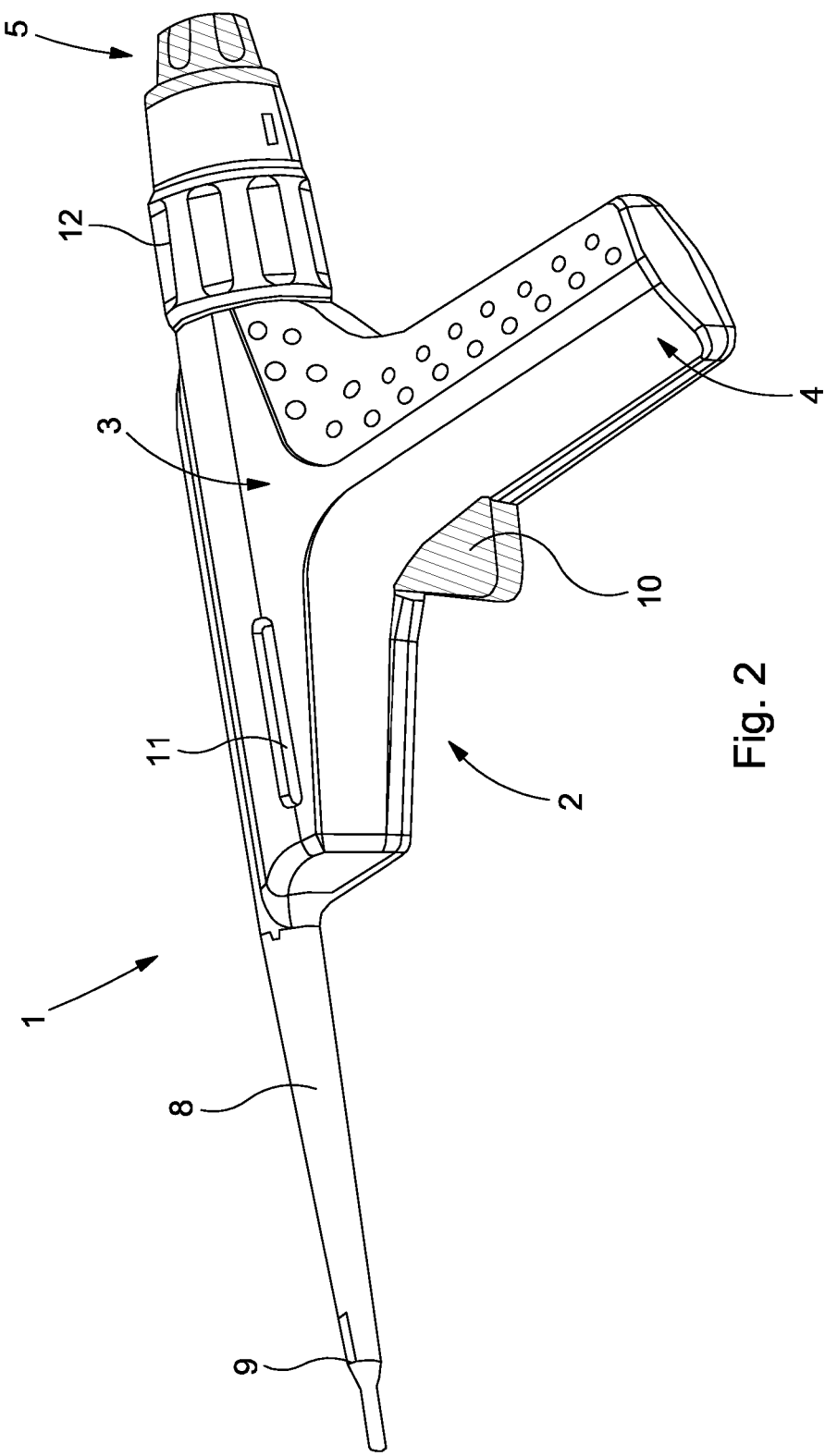
FIG. 2 is similar to FIG. 1 but shows the applicator in an activated configuration.

Referring firstly to FIGS. 1 and 2, there is illustrated therein, in two different configurations, one embodiment of adhesive actuator 1 in accordance with the invention. FIG. 1 shows the actuator 1 in an "as shipped" configuration, from which the applicator 1 requires "activation" (in the manner described in more detail below) into the configuration illustrated in FIG. 2 to allow discharge of adhesive from the applicator. As shown in FIG. 1, the applicator 1 is of generally "pistol-like" appearance and comprises a casing 2 formed as a barrel portion 3 and a handle portion 4. Provided at the right-hand end (as viewed in FIG. 1) of casing 2 is a plunger assembly 5 in which is located a sleeve 6 holding an elongate ampoule 7 containing an adhesive to be dispensed by the applicator 1 (see also FIG. 5 below and related description). Only sleeve 6 is seen in FIG. 1 and thus ampoule 7 is indicated by the dashed reference line. At the left-hand end (as viewed in FIG. 1) of the casing 2 is a cannula 8 on the distal end of which (i.e. the end remote from casing 2) is an applicator tip 9. A further feature of the applicator 1 illustrated in FIG. 1 is a trigger 10 (e.g., a first actuator) which is pivotally mounted within the casing 2 and resiliently biased to the position shown in FIG. 1 whereby the trigger 10 may be depressed and then released to allow the trigger to return to the position illustrated in FIG. 1. Matching elongate apertures 11 (only one seen in FIGS. 1 and 2) are formed on opposite sides of the barrel 3 and allow visualisation of an indicator element 313, the position of which along the window 11 is indicative of the level of adhesive remaining in the applicator. Further shown in FIG. 1 is a rotary priming knob 12 (e.g., a second actuator) which (as described in more detail more) has a function in activation of the applicator.

Viewed externally, the difference between the configurations of the applicator 1 shown in FIGS. 1 and 2 is that, in the former, the plunger assembly 5 is in an extended position whereas, in the latter, the plunger 5 has been moved to the left (as viewed in FIG. 1) so as to be in a retracted position. In use, the applicator 1 is "activated" from the configuration illustrated in FIG. 1 to that shown in FIG. 2 to allow for fracturing of the ampoule 7 and release of adhesive contained therein to a reservoir unit (to be described below) internally of the body 1. Rotation of priming knob 12 completes activation of the applicator. In the activated condition of the applicator 1 (FIG. 2), depression of the trigger 10 allows a droplet of adhesive of known volume (typically about 10-15 µl) to be discharged from the tip 9. Each subsequent depression of the trigger 10 discharges a further, single drop of the adhesive until the reservoir thereof has been depleted. Typically, the amount of adhesive in the ampoule 7 will be sufficient to allow the applicator to discharge a total of 35 drops of adhesive.

A more detailed description of the construction of the applicator 1 will now be given.

Figure 11:
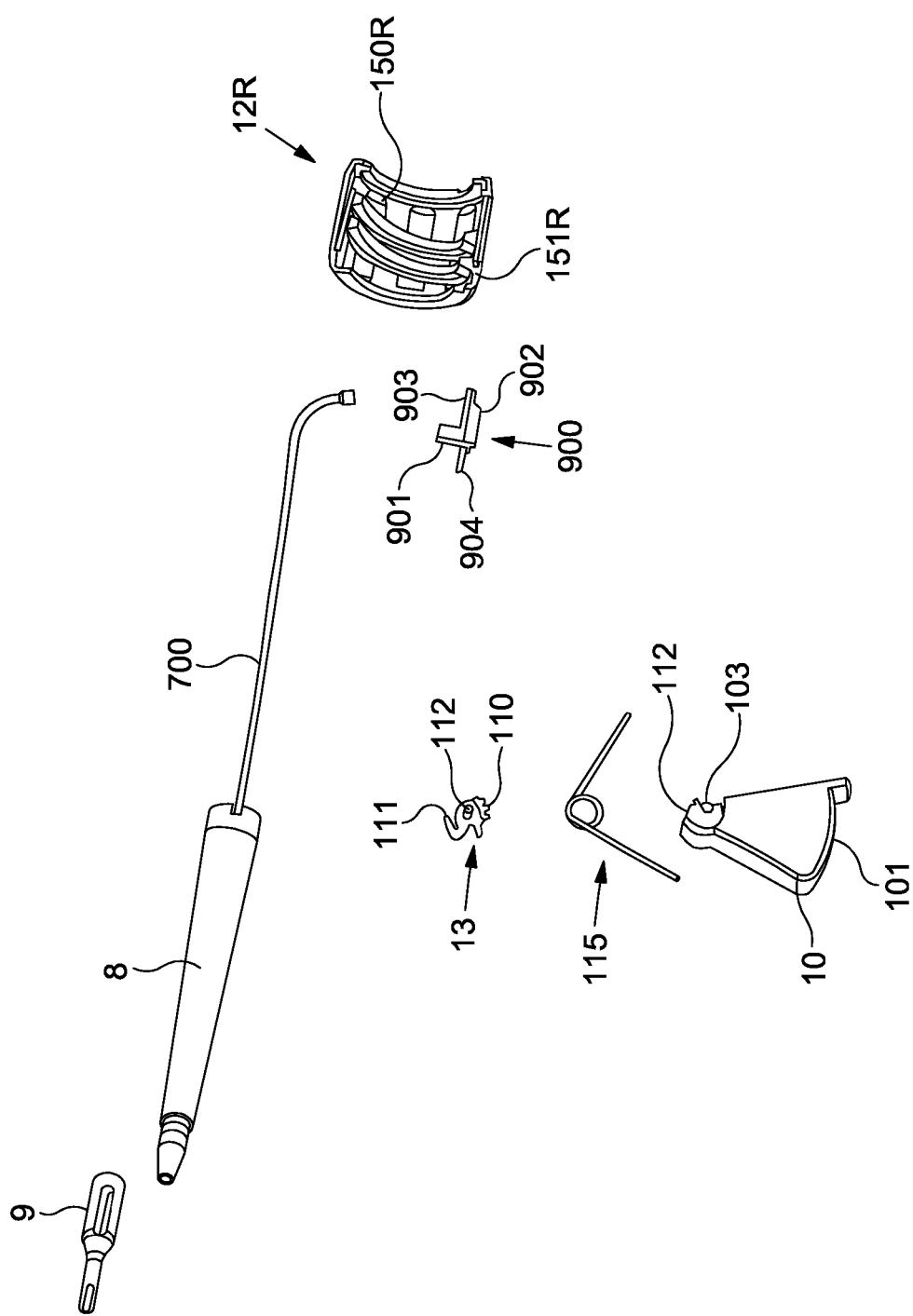
FIG. 11 illustrates further components of the applicator.
Figure 12:
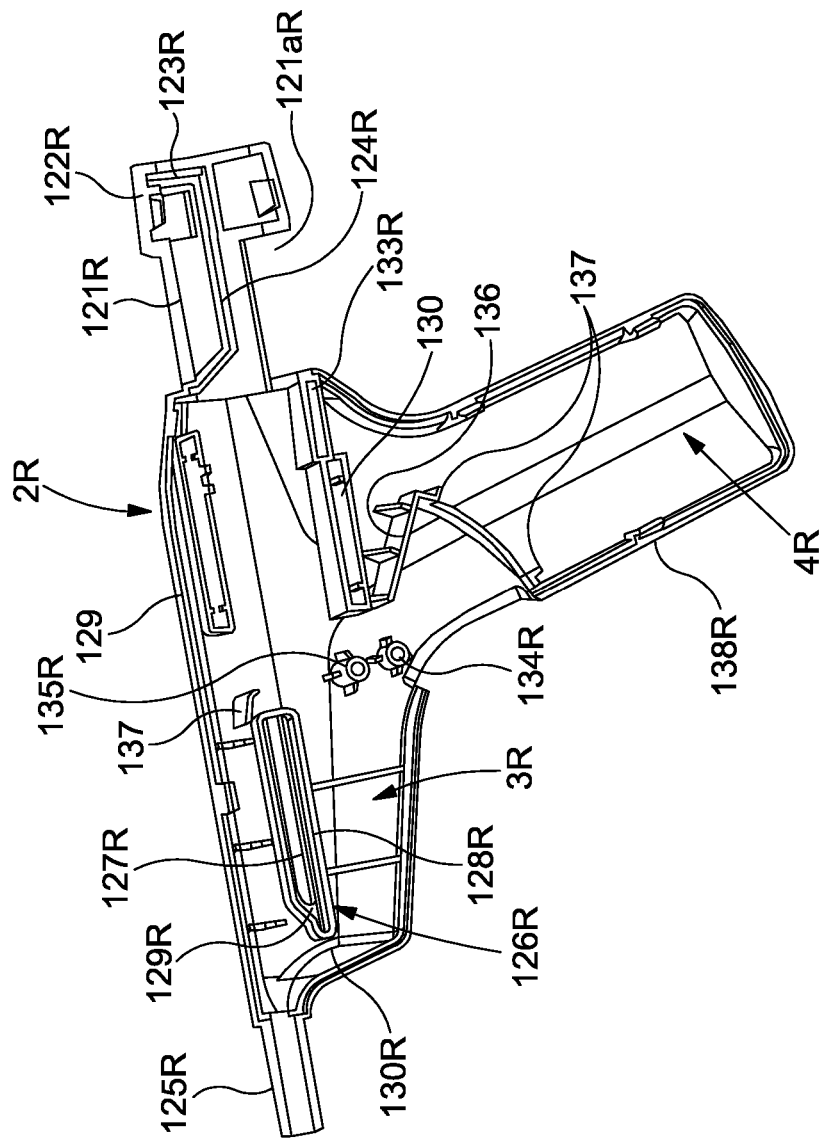
FIG. 12 shows interior detail of the right hand casing half of the applicator.

Casing 2 is formed in two longitudinally separate halves 2R and 2L (see also FIGS. 11 and 12) as is the priming knob 12 (see FIG. 12).

Figure 3:
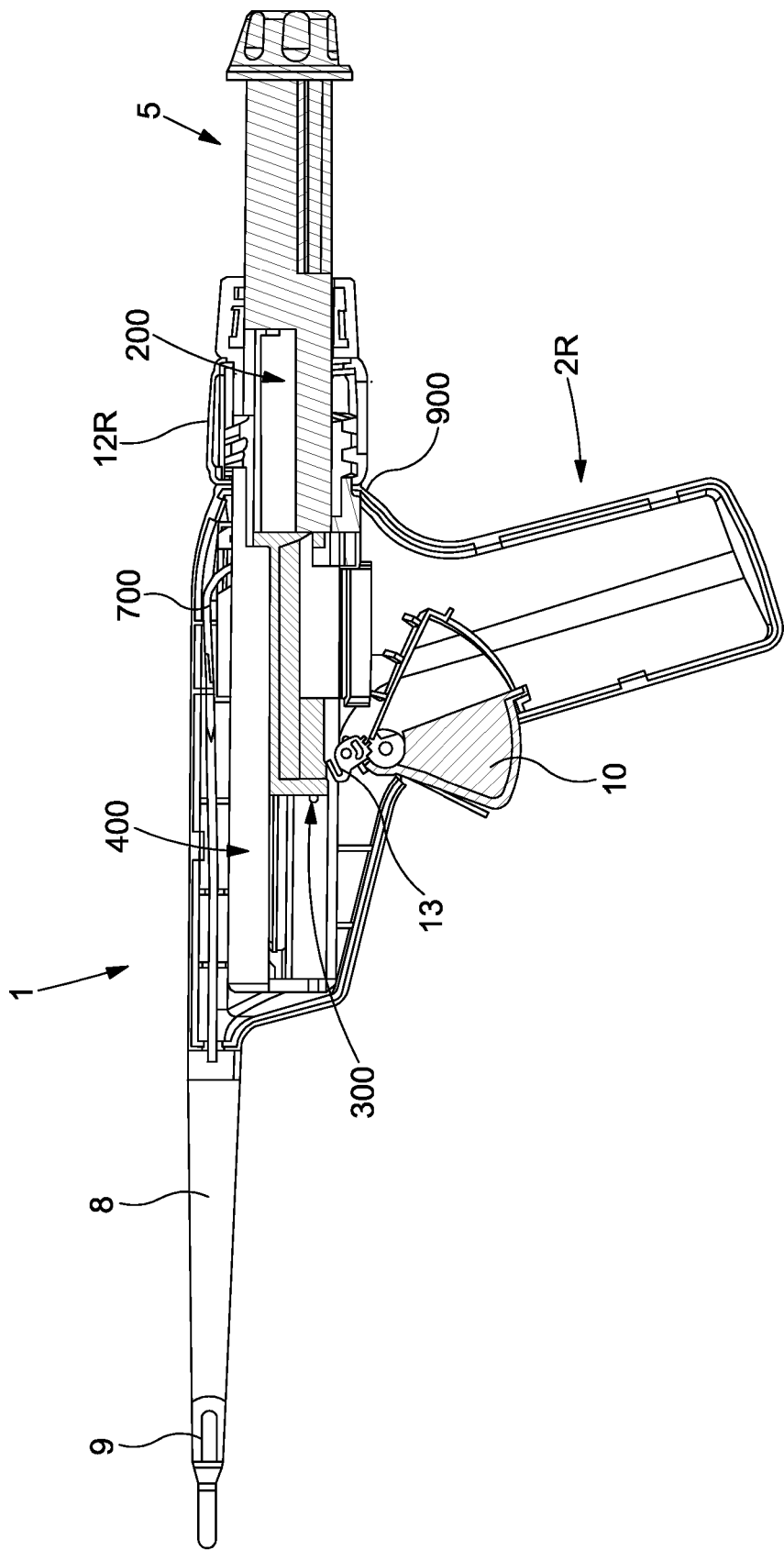
FIG. 3 is similar to FIG. 1 but with a portion of the casing of the applicator removed to reveal interior detail.
Figure 4:
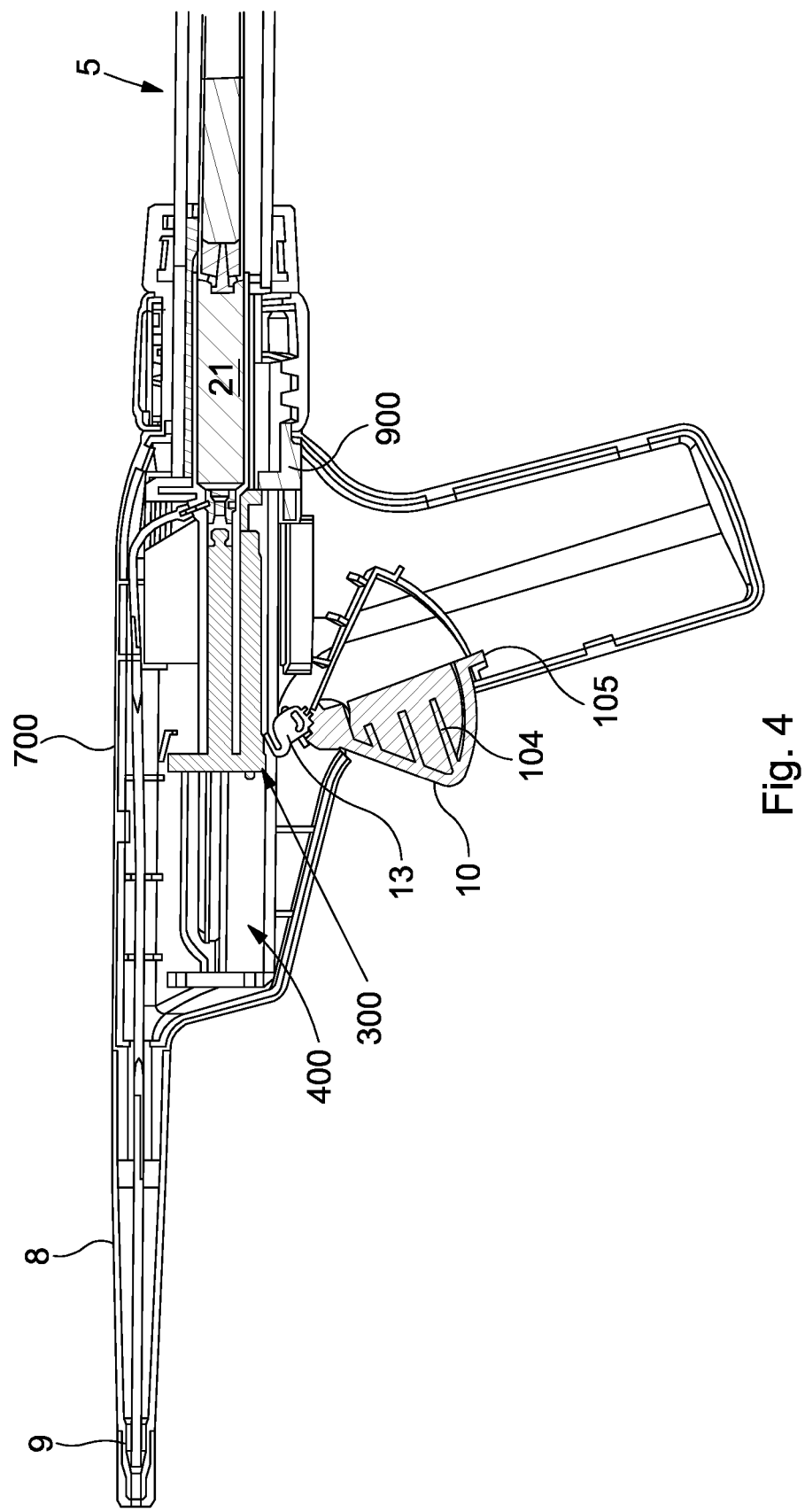
FIG. 4 is a longitudinal sectional view through the applicator in the configuration shown in FIG. 3.

FIG. 3 shows the applicator 1 in the configuration depicted in FIG. 1 but with the front halves of the casing 2 and the priming knob 12 removed to reveal interior components of the applicator 1. FIG. 4 is similar to FIG. 3 but is a sectional view taken on the longitudinal centre line of the applicator 1 to reveal further details of the interior structure thereof. Within applicator 1 are a reservoir unit 200 (including coaxial priming chamber 201 and delivery chamber 202), a delivery piston assembly 300, a priming carriage 400, a flexible delivery tube 700 that extends from reservoir unit 200 to deliver adhesive to the applicator tip 9, and a rotary pawl unit 13 operable by the trigger 10 to effect movement of the delivery piston unit 30. Also shown in FIG. 3 is a priming lock pin 900 provided to ensure that the required steps of the activation procedure must be effected in a certain sequential order (as described more fully below).

In general outline (and to be described in greater detail below) activation of the applicator 1 for delivery of adhesive is effected by the following steps. Initially, the applicator 1 (in the configuration shown in FIG. 1) is held in one hand with the cannula 8 pointing downwards. Plunger assembly 5 is then rotated to fracture ampoule 7 and allow its adhesive content to drain into the transfer chamber 201 of the reservoir unit 200. Plunger assembly 5 is then moved axially to its contracted position (FIG. 2) to effect movement of delivery piston unit 300 towards the distal end of the applicator 1 whereby a piston thereof (to be described in more detail below) which locates in the delivery chamber 202 of reservoir unit 200 draws adhesive into that chamber. The applicator 1 may now be positioned so that the cannula 8 is horizontal. During the majority of the length of the travel of the delivery piston unit 300 towards the distal end of the applicator 1, the flexible tube 700 is closed to the passage of adhesive therealong. As the delivery piston unit 300 approaches its leftmost position, the flexible tube 700 is opened to adhesive flow. In the next stage of activation (and as allowed by the configuration of the internal components of the applicator 1) the priming knob 12 is rotated causing a short movement of the priming carriage 400 to the right which in turn effects a corresponding movement to the right of the delivery piston unit 300. During this step, the aforementioned piston (of delivery piston unit 300) is effective to expel any air from the delivery chamber 202 of reservoir unit 200 along the flexible delivery tube 700 and also to fill that tube with adhesive. Once this stage has been reached (and only at this stage) trigger 10 becomes effective to operate pawl unit 13 to advance delivery piston unit 300 incrementally to the right (one increment of movement for each squeeze of the trigger 10) resulting in discharge of one drop of adhesive from the applicator tip 9. Further points to be noted (and to be described more fully below) are interlock features of the applicator 1. When in the "as supplied" configuration illustrated in FIG. 1, the described axial movement of the plunger assembly 5 can only be effected after rotary movement thereof to fracture the ampoule 7. During this rotary movement of plunger assembly 5, the priming knob 12 is locked against rotation by the priming lock pin 900—therefore initially only rotary movement of the plunger assembly 5 is permitted. At the limit of its rotational movement, plunger assembly 5 may be moved axially to the left (as described above). During this axial movement, priming knob 12 remains locked against rotary movement by priming lock pin 900. At the limit of its axial movement, plunger assembly 5 displaces priming lock pin 900 to a position that prevents rotary movement of plunger assembly 5 but now permits rotary movement of priming knob 12 (for movement of priming carriage 900 as described above).

It should be appreciated at this stage that only a brief outline of the operation of applicator 1 has been given and this is to facilitate an understanding of the more detailed description given below of the various components that interact to allow activation of the applicator 1 and delivery of adhesive.

Figure 5:
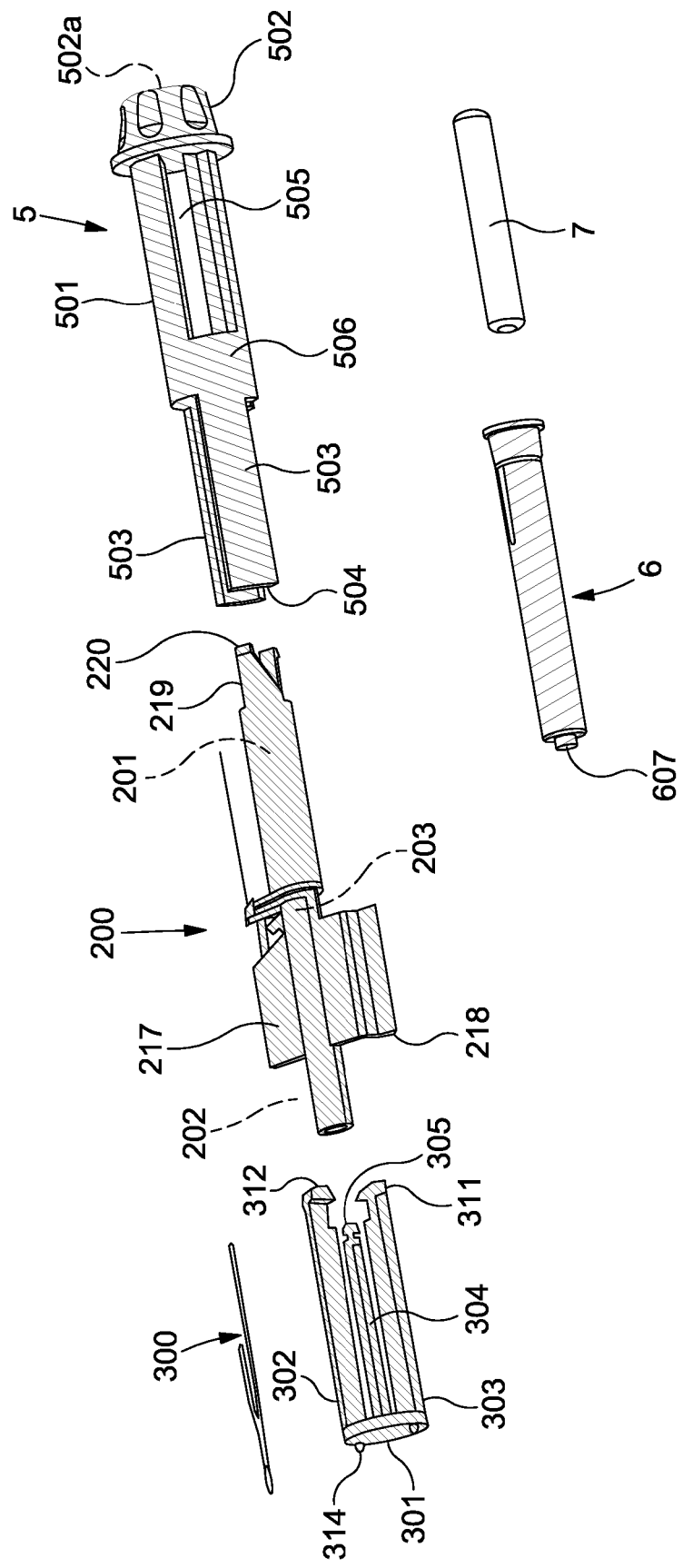
FIG. 5 shows details of internal components of the applicator.

Reference is now made to FIG. 5 for a more detailed description of components of the applicator 1.

As seen in FIG. 5, plunger assembly 5 comprises a generally cylindrical body portion 501 at the right-hand end of which (as viewed in FIG. 5) is a knob 502 and at the left-hand end of which are two elongate fingers 503, both of which have the same radius of curvature as the body portion 501, these two fingers 503 being diametrically opposed to each other and separated by elongate gaps 504. Formed in the body portion 501 are two elongate, windows 505 that extend axially parallel to the plunger assembly 5.

Figure 6:
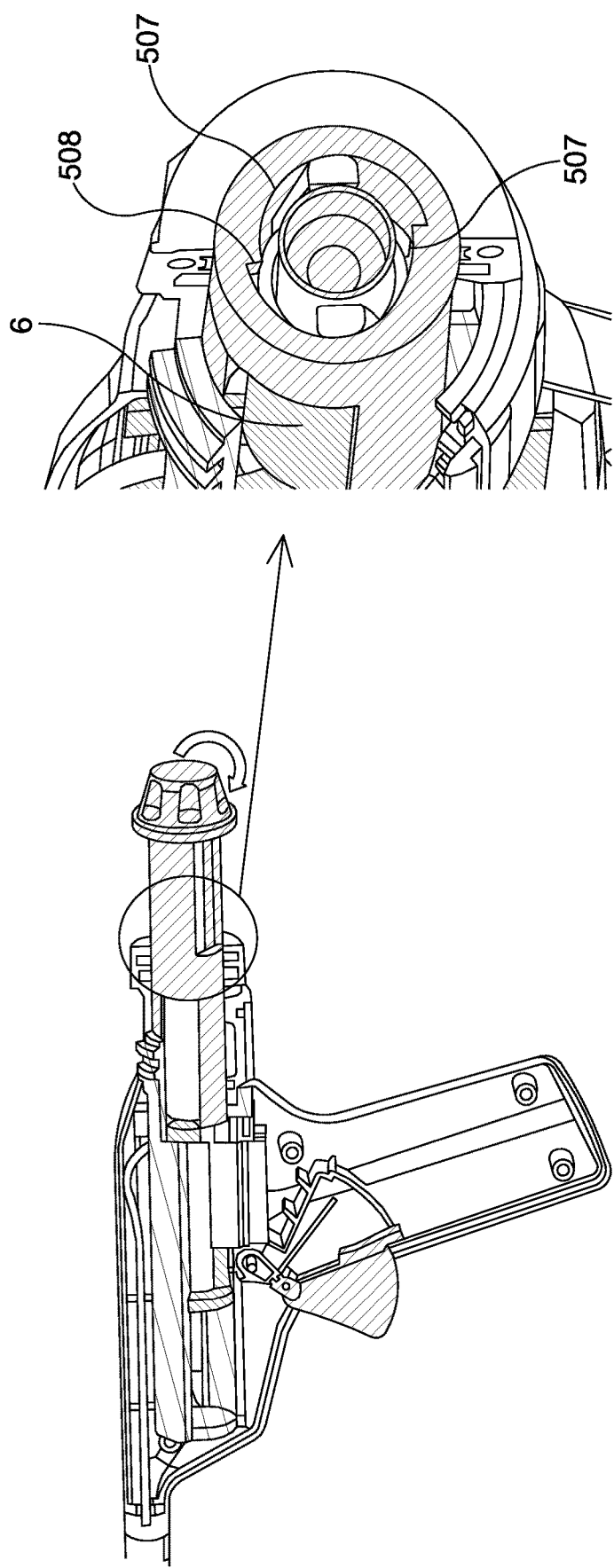
FIG. 6 illustrates details of the mechanism in the applicator for fracturing an ampule.

These windows 505 permit viewing of the sleeve 6 (containing ampoule 7) when applicator 1 is in the configuration shown in FIG. 1. On the body portion 501, are two diametrically opposed pins 506 (only one seen in FIG. 5). A further feature of plunger assembly 5 (see FIG. 6) are two internal cam surfaces 507 each extending in a generally circumferential direction partway around the interior surface of body portion 501 between the right-hand ends of fingers 503 and the left-hand ends of windows 505. These cam surfaces 507 are not visible in FIG. 5 but (as indicated) can be seen in FIG. 6, which is a sectional view through the applicator taken between the adjacent ends of the windows 505 and fingers 503. It will be appreciated from FIG. 6 that the cam surfaces 507 are configured to provide a rotary camming action on rotation of the plunger assembly 5. Also as illustrated in FIG. 6, camming surfaces 507 are terminated by steps 508.

502 is a generally hollow structure closed by an end face 502a in which is formed a small diameter breather hole (not illustrated in FIG. 5) which is attached to, and in communication with, a breather tube (again not seen in FIG. 5) that extends inwardly of the knob 502 part way along the axial centre line of the plunger assembly 5.

Plunger assembly 5 serves inter alia to hold sleeve 6 which contains ampoule 7, both illustrated in FIG. 5. Ampoule 7 is of a conventional type and comprises a frangible material (e.g. glass), the ampoule holding a charge of curable adhesive material (typical a cyanoacrylate adhesive formulation). Sleeve 6 is of generally hollow cylindrical construction, being open at its right-hand end (to permit insertion of the ampoule 7) and being closed at its left-hand end with a coarse filter unit 601 (moulded as part of the sleeve 6) which can be seen in the enlarged view of FIG. 7. This filter unit 601 is formed with filtration apertures 602 and further has on its face remote from the interior of sleeve 6 a nose 603 and on its opposed face a prong 604 projecting towards the ampoule 7 and it its end is in contact therewith. This prong 604 serves to assist in retaining ampoule 7 in position, the other end of the ampoule 7 being located against the free end of the aforementioned breather tube.

Figure 7:
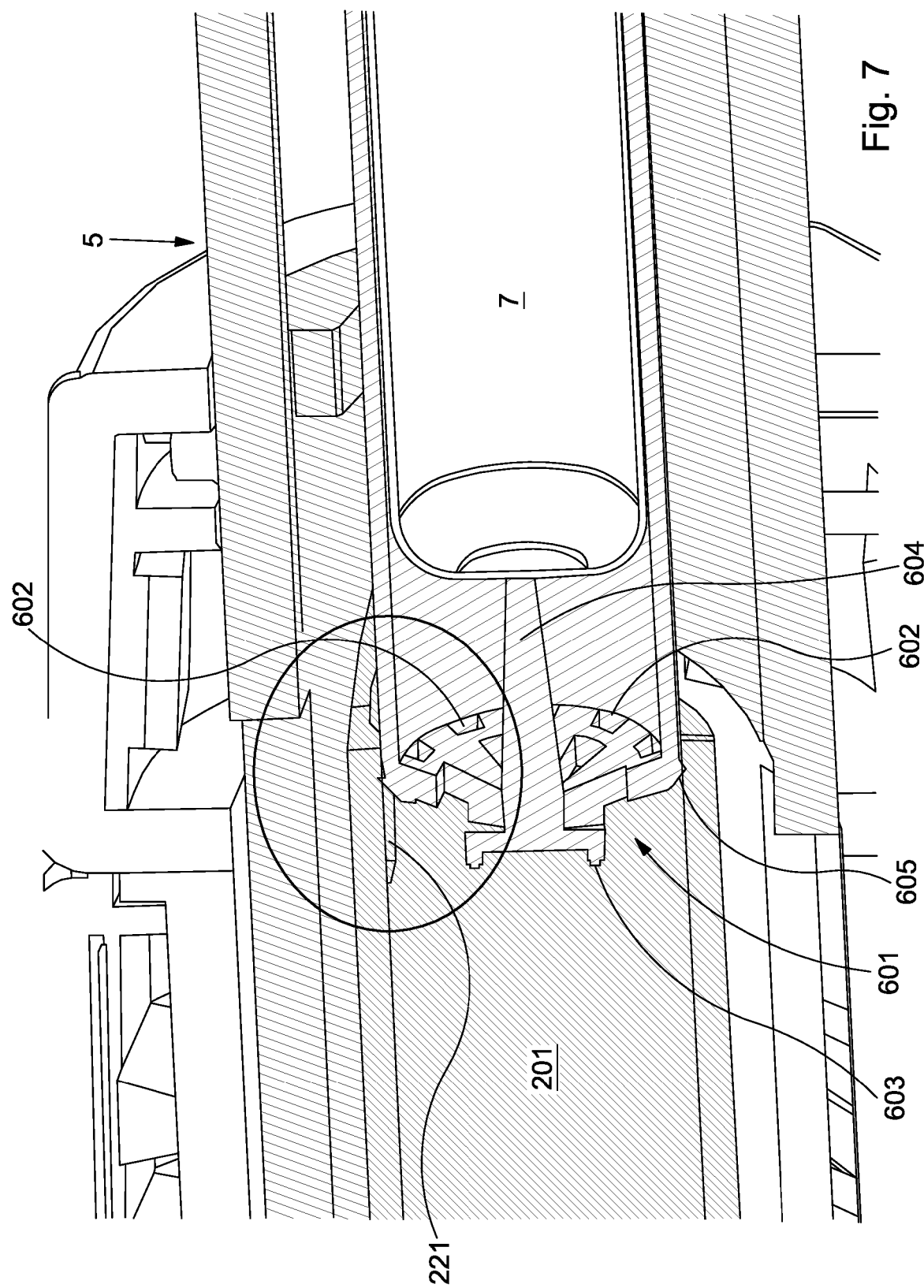
FIG. 7 shows (to a much enlarged scale) an internal detail of the priming chamber and sleeve (holding the ampule) of the applicator.

Furthermore, as show in FIG. 7, a flange 605 extends around and projects radially from the outside peripheral surface of coarse filter unit 601.

Filter unit 601 derives its filtering characteristics from the apertures 602 that surrounds the nose 603 and prong 604. These apertures 602 are dimensioned to filter out relatively large pieces of glass resulting from fracturing of the ampoule to ensure that these relatively large pieces do not pass to the transfer chamber 201 (and thus not to the delivery chamber 202). Filtration of finer components of glass is effected by an additional filter described below.

It will be appreciated that, during assembly of the applicator 1, the ampoule 7 is inserted into the free end of sleeve 6 and this combination is then inserted between the fingers 503 into the plunger assembly 5. With the sleeve 6 fully inserted in position, the right-hand end of ampoule 7 locates against the free end of the aforementioned breather tube, whereby ampoule 7 is retained axially in position by virtue of being located in contact both with the prong 604 (in filter unit 601) and the breather tube.

Figure 8:
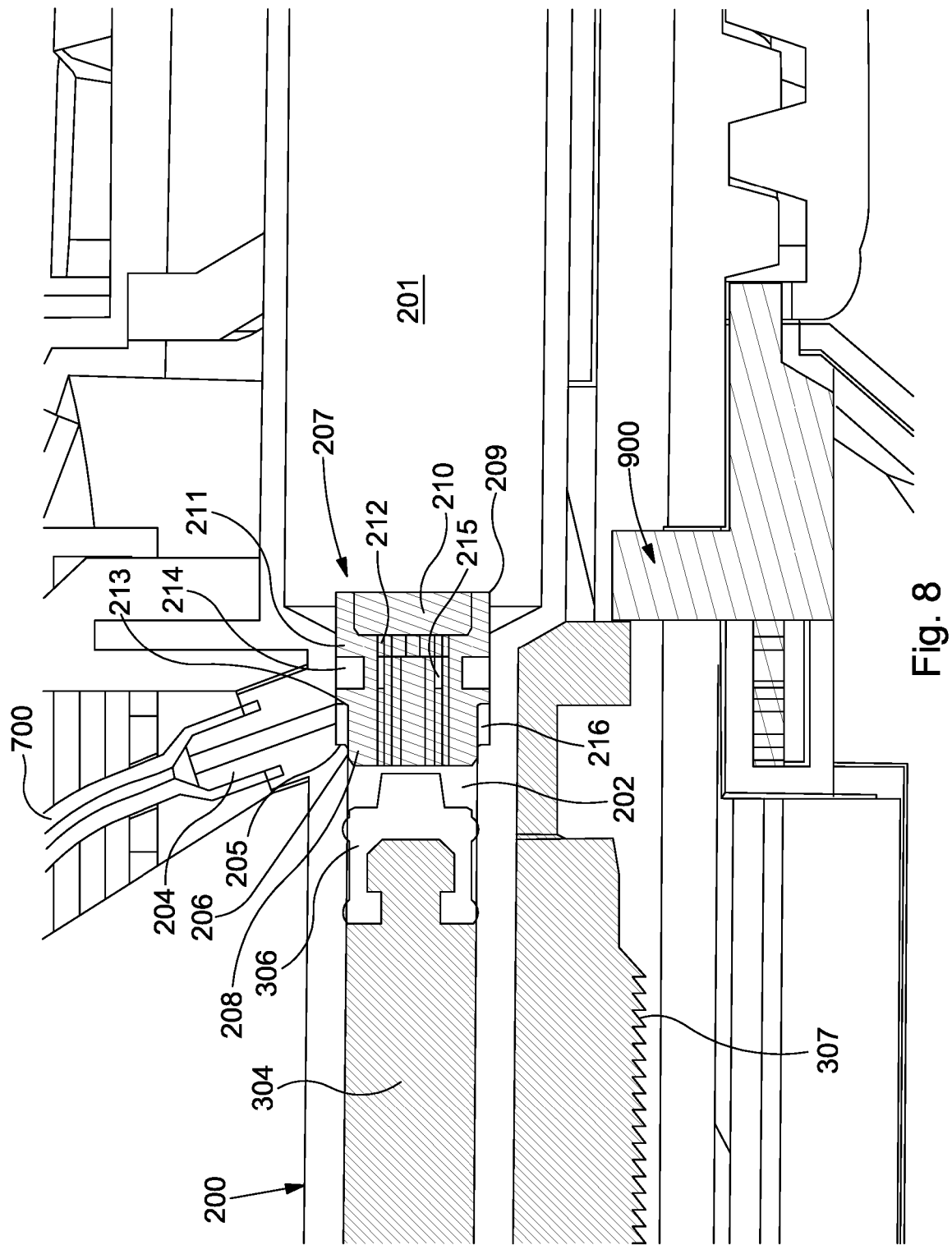
FIG. 8 shows a detail of the priming, delivery and intermediate chambers of the applicator, with the piston in a position of readiness for drawing adhesive into the priming chamber and the adhesive outlet being closed to fluid flow.
Figure 9:
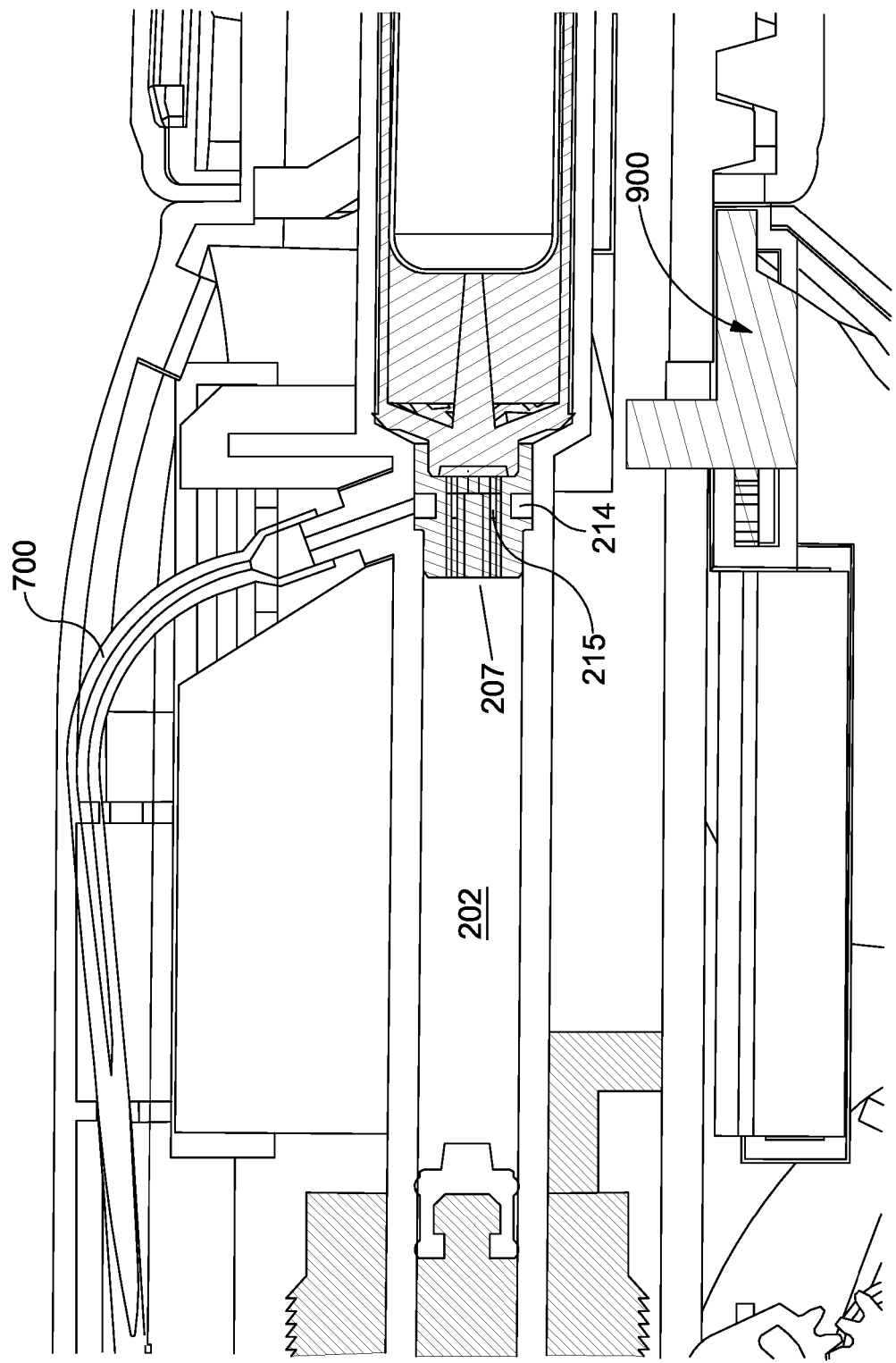
FIG. 9 is similar to FIG. 8 but shows the piston having been moved to draw adhesive into the priming chamber and the adhesive outlet being open to fluid flow.

Reference is now made to the reservoir unit 200 which is seen, in perspective view, in FIG. 5 and in the sectional views in FIGS. 8 and 9. Reservoir unit 200 is of elongate, generally tubular construction and (as indicated) is internally sub-divided into a transfer chamber 201 (the right-hand chamber as seen in FIG. 5) and a coaxial delivery chamber 202 (the left-hand chamber as seen in FIG. 5). Provided between the left-hand end of transfer chamber 201 and the right-hand end of delivery chamber 202 is an intermediate chamber 203 from which leads an adhesive outlet 204 connected to the upstream end of flexible tube 700. Intermediate chamber 203 is of constant diameter along its length and is of greater diameter than delivery chamber 202 but lesser diameter than the majority of the length of transfer chamber 201. More specifically, an annular step 205 at the interface of intermediate chamber 203 and delivery chamber 202 (and facing towards the intermediate chamber 203) provides for the variation in diameter as between these two chambers. Additionally, transfer chamber 201 converges at its end adjacent to intermediate chamber 203 to provide for the transition in diameters between these two chambers (sees FIGS. 8 and 9).

Also shown in FIGS. 8 and 9 is an annular nib 206 formed on the radially inner end of step 205 and projecting into the right-hand end of delivery chamber 202.

Provided in intermediate chamber 203 is a fine filter unit 207 which comprises a downstream tubular body portion 208 and an upstream annular head 209 with a recess 210, these components being mounted on (and either side of) a filter plate 211 formed with fine filtration apertures 212.

Body portion 208 of fine filter unit 207 is formed with an annular flange 213 having an exterior diameter equal to the internal diameter of intermediate chamber 203 and being spaced from the filtration plate 211 whereby an annular groove 214 is defined between opposed faces of flange 213 and filtration plate 211. On the left-hand side of flange 213, body portion 208 has an exterior diameter corresponding with the interior diameter of the annular nib 206 that projects radially inwardly from step 205.

Formed in the floor of the annular groove 214 are a plurality of circumferentially spaced adhesive transfer apertures 215 that provide communication between the groove 214 and the interior of tubular body portion 208 of filter unit 207

FIG. 8 illustrates the position of the fine filter unit 207 in the configuration of the applicator 1 illustrated in FIG. 1 (i.e. prior to activation of the applicator). In the position of the fine filter unit 207 illustrated in FIG. 8, it will be noted that the adhesive outlet 204 is in communication with an annular groove 216 defined at its radially inner and outer sides by the exterior surface of tubular body portion 208 and interior surface of the intermediate chamber 203 respectively and defined at its axial ends by the annular flange 230 and the step 205. As such, the fine filter unit 207 closes the adhesive outlet 204. A further point to note is that the internal diameter of the recess 210 in head 209 is capable of accommodating the nose 603 of sleeve 6 as a close fit.

FIG. 9 illustrates the position of the fine filter unit 207 in the configuration of the applicator 1 illustrated in FIG. 2 (i.e. after activation). In this configuration, adhesive outlet 204 is in communication with the annular recess 214 which in turn communicates with the delivery chamber 202 via the adhesive transfer apertures 215. As such, adhesive may be passed from the delivery chamber 202 to the adhesive outlet 204.

Additional features of the reservoir unit 200 seen in FIG. 5 are a pair of diametrically opposed wings 217 extending radially from the exterior of delivery chamber 202, the wings 217 having axially parallel tabs 218 provided on their undersurfaces at the radially outer ends thereof, these tabs being provided for the purpose of locating the reservoir unit 200 in position within the applicator 1. Additionally, the upstream end of transfer chamber 201 is provided with a pair of diametrically opposed breaker tabs 219 which are thickened as illustrated at their free ends, as depicted by reference numeral 220. These tabs 219 are capable of being flexed inwardly towards each other to effect breakage of the ampoule 7 in the manner described below. A further feature of the delivery chamber 201 (seen in FIG. 7) axially parallel grooves 221 formed in the interior wall of transfer chamber 202 at the end adjacent tabs 219. As further seen in FIG. 7, the circumferential flange 605 (of sleeve 6) has an exterior diameter corresponding to the interior diameter of the transfer chamber 202 so that there is clearance between the flange 605 and the surfaces of the grooves 221.

Reference is now made to delivery piston unit 300 (see FIGS. 5 and 6). This unit comprises, at one end, circular plate 301 from which project, from two diametrically opposed locations on a face thereof, two generally parallel arms 302 and 303, with there being a central arm 304. Central arm 304 is of shorter length than arms 302 and 303 and has a head portion 305 on which a seal 306 (not seen in FIG. 5 but see FIGS. 8 and 9) is fitted. The combination of arm 304 and seal 306 together provide a piston dimensioned (and spaced from the arms 302 and 303) such that it may be inserted into the delivery chamber 202 (of the reservoir 200) with the seal 206 as a close sliding fit therein (see FIGS. 8 and 9).

On their radially outer surfaces, the arms 302 and 303 each have a set of ratchet teeth 307 and 308 respectively (see FIGS. 8 and 9) that extend from respective plain portions 309 and 310 at the free ends of arms 302 and 303. Going towards the circular plate 301, the ratchet teeth 307 and 308 extend to a location just short of the circular plate 301. Extending from the free ends of the arms 302 and 303 are generally L-shaped contact members 311 and 312 respectively, the purpose of which will be described below.

Two diametrically opposed pins 313 project radially from the circumferential surface of the circular plate 301 at locations mid-way between the arms 302 and 303. Two further pins 314 project from the end face of circular plate 301 opposite the arms 301-303. A line joining the two pins 303 is perpendicular to a line joining the pins 304.

Priming carriage 400 is shown in FIG. 10 and comprises two elongate arms 401 affixed to a circular base plate 402. Base plate 402 is of greater diameter than plunger assembly 5 and the arms 401 are arcuate as seen in transverse cross-section with the internal radius of the arms 401 being equal to that of the base plate 402. As such, plunger assembly 5 may be received between the arms 401. Arcuate fingers 403 (having the same radius as the arms 401 and having one edge colinear therewith) extend from the arms 401 as shown and have on their external surfaces and towards their free ends part helical projections 404 as illustrated providing a screw-thread function. Fingers 403 are of lesser arcuate width than arms 401 and are offset from each other, as illustrated in FIG. 10. Since the fingers 403 are of lesser arcuate width than arms 401, ledges 405 are defined at the ends of the arms, as seen in FIG. 10. Additionally, each finger 403 is formed on its edge that is collinear with an edge of arm 401 with a step 406 (of lesser height than ledge 405), each step 406 being located between the part helical formation 404 and the end of arm 401. Base plate 402 of primer carriage 400 is formed with two diametrically opposed apertures 407 capable of receiving the pins 314 projecting from the face of circular plate 301 of piston unit 300.

The trigger 11 is shown in FIG. 11 (and see also the sectional view of FIG. 4) and will be seen to be of generally triangular construction with one arcuate side 101 at the opposite apex to which ratchet teeth 102 are provided for operative engagement with the rotary pawl unit 13. Furthermore, at this apex, there are two coaxial pins 103 projecting from opposite faces of the trigger 10 and provided for pivotal mounting of the latter in the applicator 1. As best seen in FIG. 4, trigger 10 is of hollow-shell construction and has one open side (the right-hand side as viewed in FIG. 4) and a plurality of internal ribs 104 that extend towards, but short of, the open side of the trigger. A stop flange 105 is provided at the end of the arcuate side 101 adjacent to the open side of the trigger.

Pawl unit 13 (see FIG. 11) has a set of ratchet teeth 110 for cooperation with ratchet teeth 102 of trigger 10 and also has a pawl 111 for engagement with the ratchet teeth 307 (or 308) on arm 302 (or 303) of delivery piston unit 300. Furthermore, pawl unit 13 is provided with two opposed projecting pins 112 for the purpose of pivotally mounting pawl unit 13 in the applicator 1.

Also shown in FIG. 12 is wire spring 115 of generally V-shaped configuration, the spring being coiled at its apex and serving for resilient biasing of the trigger 10 to its position as shown in FIG. 1.

Figure 13:
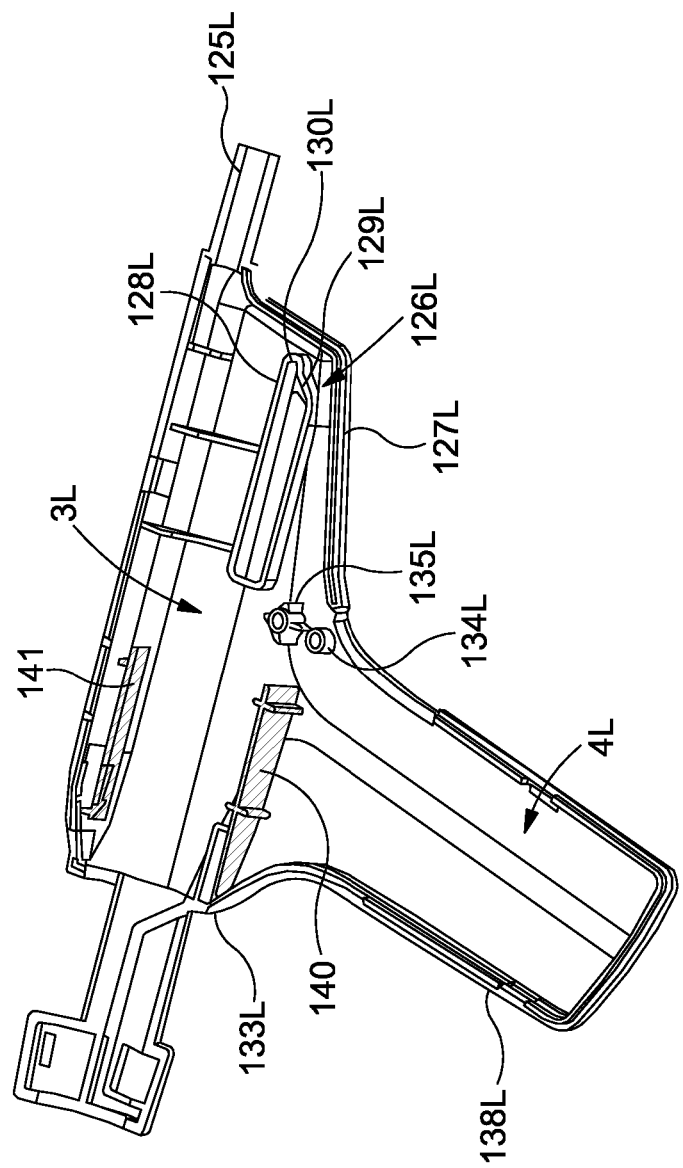
FIG. 13 shows a detail of the left hand casing half of the applicator.

Reference is now made to FIGS. 12 and 13 which respectively show the interior configurations of the right and left halves of casing 2. In this context, the "right half" of the casing is that half which is at the right hand side of the applicator when the latter is viewed from the proximal end thereof (i.e. looking from the plunger assembly 5 towards the cannula 8). The two body casing portions (designated 2R and 2L) are, in many (but not all) respects, mirror images of each other. Like parts in the two body casing portions are, for convenience, identified by the same reference numeral but suffixed by "R" (for right) or "L" (for left) as appropriate. Initially, a description of body casing portion 2R will be given, followed by a description of body casing portion 2L to the extent that it differs.

Considering firstly the right-hand casing portion 2R (FIG. 12), this will be seen to comprise barrel and handle portions 3R and 4R respectively which when mated with corresponding portions 3L and 4L of the left-hand casing portion together form the barrel 3 and handle 4 for the applicator 1. Casing portion 2R further comprises a neck portion 121R terminated by an enlarged head 122R. Casing portion is less than semi-circular in extent, whereby a "cut-away" 121aR is defined as shown. Extending circumferentially around the interior of enlarged head 122R is a groove 123R which, at one end, joins with a groove 124R that (going in the direction from the head portion 122R to the barrel portion 3R) initially extends linearly along the interior of neck portion 121R and then (as seen in FIG. 12) inclines upwardly around the interior surface of neck portion 121R. A further consideration of the function of the grooves 123R and 124R will be given below.

At the opposite end of body casing 2R to the neck portion 121R is a spigot portion 125R (which will mate with the corresponding spigot portion 125L of casing portion 2L to form a spigot on which cannula 8 may be mounted).

Within casing portion 2R is a guide track unit 126R having upper and lower runs 127R and 128R respectively, these two runs being connection by an inclined transition region 129R towards the distal end of guide unit 125R. Just to the left (as seen in FIG. 12) of transition region 129R is a detent region 130R. Further consideration of the function of the guide track unit 125R will be given below.

Also within right-hand casing portion 2R are two rectangular location housings 129 and 130 which serve to locate the tabs 218 on the under surfaces of the wings 217 of reservoir unit 200. A further rectangular location housing 133R is provided to accommodate the priming lock pin 900. A further feature of right-hand casing portion 2 is a wall 136 (against which a leg of spring 115 will act) and two tabs 137 for limiting travel of the trigger 10 (in either direction) by virtue of interaction with flange 105 on the trigger.

Additionally included in casing portion 2R are two hollow cylindrical mounting pillars 134R and 135R which are intended to receive pins 103 and 112 of the trigger 10 and pawl unit 13 respectively.

A pawl 137 is provided as shown in the upper region of barrel portion 3R.

Finally, the casing portion 2R is provided at various locations around its periphery with snap fastener formations 138R for cooperation with complementary snap fastener formations 138L on body casing portion 2L to allow the two body casing portions to be snap fitted together.

Referring now to body casing portion 2L, this is (as indicated) generally a mirror image of body casing portion 2R. There are however differences to note. Guide track unit 126L is configured not to be an actual mirror image of guide track unit 126R but rather with run 128R to be above 127. A further difference lies in the fact that body casing portion 2L does not have the rectangular housing units 131 and 132 which are for the purpose of accommodating the tabs 218 on the underside of the wings 217 of the reservoir unit 200, but rather have elongate fins 140 and 141 for acting against the upper surfaces of the wings 217 of the reservoir unit 200. Additional differences are that casing portion 2L does not have counterparts to the pawl 138, the wall 136 or the tabs 137.

Reference is now made to the cannula 8 and nozzle 9 (see FIG. 11). Nozzle 9 is a removable fit on the distal end of cannula 8 and is configured for applying small droplets of adhesive to a tissue site in the body. The distal end of cannula 8 is also configured as an applicator tip, but in this case one that is capable of applying a broader stripe of adhesive than the nozzle 9. Flexible delivery tube 700 is also seen in FIG. 12 and extends to the distal tip of cannula 8.

Priming knob 13 is formed in two halves, 13R and 13L (the former being shown in FIG. 11). As illustrated, priming knob half 13R is generally semi-circular and is formed with two part helical projections 150R as seen in FIG. 12. These part helical projections 150R have a screw thread function and are complementary with the helical projections 404 on priming carriage 400. Priming knob half 13R has a small notch 151R towards the end of one of its arcuate edges. Priming knob half 13L is almost a mirror image of priming knob half 13R but lacks the equivalent of notch 151R.

Priming lock pin 900 is shown in FIG. 11 and comprises a generally L-shaped component with a short leg 901 and a longer leg 902 formed at its free end with a locking projection 903 which is intended to locate in the aperture of the assembled priming knob 13. On its side remote from the longer leg 902, the priming locking pin is provided with a living hinge 904.

Assembly of the applicator 1 will now be described. The components illustrated in FIG. 5 may initially be assembled together. More specifically, ampoule 7 is inserted into sleeve 6 which is then inserted (open-end first) into plunger assembly 5 sufficiently far that the ampoule 6 is in contact with the breather tube within knob 502. In the next step of assembly, the central arm 304 (fitted with seal 306) of piston assembly 300 is inserted into the delivery chamber 202 of reservoir unit 200 such that the arms 302 and 303 lie outside delivery chamber 202 between the wings 217. Central arm 304 is inserted fully far into the delivery chamber 202, at which point the left-hand end of the latter locates with minimal clearance from the circular base plate 301. Additionally, the priming chamber 201 of reservoir unit 200 is inserted between the arms 503 of plunger assembly 5. Also an end of the flexible tube is fitted on to the adhesive outlet 2014. The assembly thus produced is then inserted between the elongate arms 401 of the priming carriage 400. This assembly of components (plunger assembly 5, reservoir unit 200, piston unit 300 and priming carriage 400) may now be inserted into casing portion 2R (see also FIGS. 3 and 4). For this purpose, the pins 506 on plunger assembly 5 are located in the part circular groove 123R in the head portion 122R of body casing portion 2R. Furthermore, one of the pins 313 that project radially from the circular base plate 301 of piston unit 300 locates in the transfer run 127R of the guide track unit 126R. Additionally, the tube 700 may be pressed into a groove (not referenced in the drawing) formed along the upper edge of barrel portion 3R of right hand casing half 2R. The tube 700 (which at this stage does not have a nozzle fitted thereto) is of a length so as to project a short distance beyond the free end of spigot portion 125R. Additional points to be noted about the assembly of the device as thus far described, are as follows. Firstly, the pin 506 on the plunger assembly 5 is located in a portion of the part circular groove 123R remote from the straight groove 124R. Secondly, the rotational position of the piston unit 300 is such that pawl unit 13 (when fitted in the manner described below) and the pawl 139 on casing half 2R both locate to one side of the ratchet teeth provided on the arms 302 and 303 of the piston unit 300. Thirdly, the part helical formations 404 on the exterior of the fingers 403 of the priming carriage 400 locate within the neck portion 121 with these helical projections being accessible (from externally of the neck portion 121R by virtue of the "cut-away" 121aR). Fourthly, the circular base plate 402 of priming carriage 400 locates at the distal end of barrel portion 3R. Fifthly, tabs 218 on the wings 217 of reservoir unit 200 are located in the rectangular housings 129 and 130 of casing portion 2R.

The trigger 10, spring 115, and rotary pawl unit 13 may now be fitted in position. For this purpose, the core portion of V-shaped spring 115 may be fitted over mounting pillar 134R and a pin 103 of the trigger then located in that mounting pillar such that one leg of the spring acts against flange 136 and the other leg acts against the free ends of internal ribs 104. Pawl unit 13 may be fitted in position in the manner that will be appreciated from FIG. 3. As indicated above, the assembly at this stage is such that the pawl unit 13 is out of engagement with any ratchet teeth on the piston unit 300.

The right-hand half 13R of priming knob 13 may now be located around the neck portion 121R with the helical projections 150R in engagement with the helical projections 404 of priming carriage 400. Priming locking pin 900 may now be located in rectangular housing 133R and positioned such that its living hinge 904 urges locking pin 900 to the right (as seen in FIGS. 3 and 4) and such that the locking projection 903 locates in the notch 151R of priming knob half 13R.

At this stage, casing portion 2L may be snap fitted to casing portion 2R to complete assembly of the casing. It should be noted that, what was previously the free radially extending pin 312 on circular base plate 301 of piston unit 300 now locates in the priming run 127L of the guide track unit 126L.

The cannula 8 (with nozzle 9) may now be fitted in position on the spigot formed by assembly of the casing halves. A groove in the cannula (not shown) aligns with a rib (also not shown) on the spigot to prevent rotation of the cannula. This allows nozzle 9 to be in the form of a "twist-off" tip that can easily be removed as required.

Operation of the applicator 1 will now be described.

As described above, applicator 1 is supplied in the configuration shown in FIG. 1. FIG. 3 shows the applicator 1 in this configuration but with the front casing removed. FIG. 4 shows a longitudinal sectional view of the applicator in the "as supplied" configuration. In this configuration, and as described above, fine filter unit 207 closes the adhesive outlet 204 to adhesive flow (see FIG. 8). The first step in activation of the applicator is a rotation of plunger assembly 5 from the configuration shown in FIGS. 3 and 4. This rotational movement is allowed by virtue of the pins 506 on plunger assembly 5 travelling around the grooves 123R and 123L until further rotary movement of plunger assembly 5 is no longer possible (the pins 506 having reached the entrance to the grooves 124R and 124L. During the rotary movement, the camming surfaces 507 are effective to move tabs 219 (of reservoir unit 200) radially inwards so as to deform sleeve 6 and fracture the ampoule 7 (see FIG. 6). As indicated above, this rotary movement of the plunger assembly 5 is effected with the applicator 1 orientated so that the cannula 8 is pointing downwards. As a result of fracture of the ampoule 7, adhesive runs downwards through the coarse filter unit 601 into the priming chamber 201. Coarse filter unit 601 is effective to prevent relatively large shards from the fractured ampoule passing into the priming chamber 201.

During the rotational movement of plunger assembly 5, primer locking pin 900 remains engaged with the priming wheel 13, thus preventing rotation thereof.

At the end of the rotational movement, the free ends of the arms 503 on plunger assembly 5 are aligned with the L-shaped contact members 311 and 312 on the piston unit 300.

Figure 14:
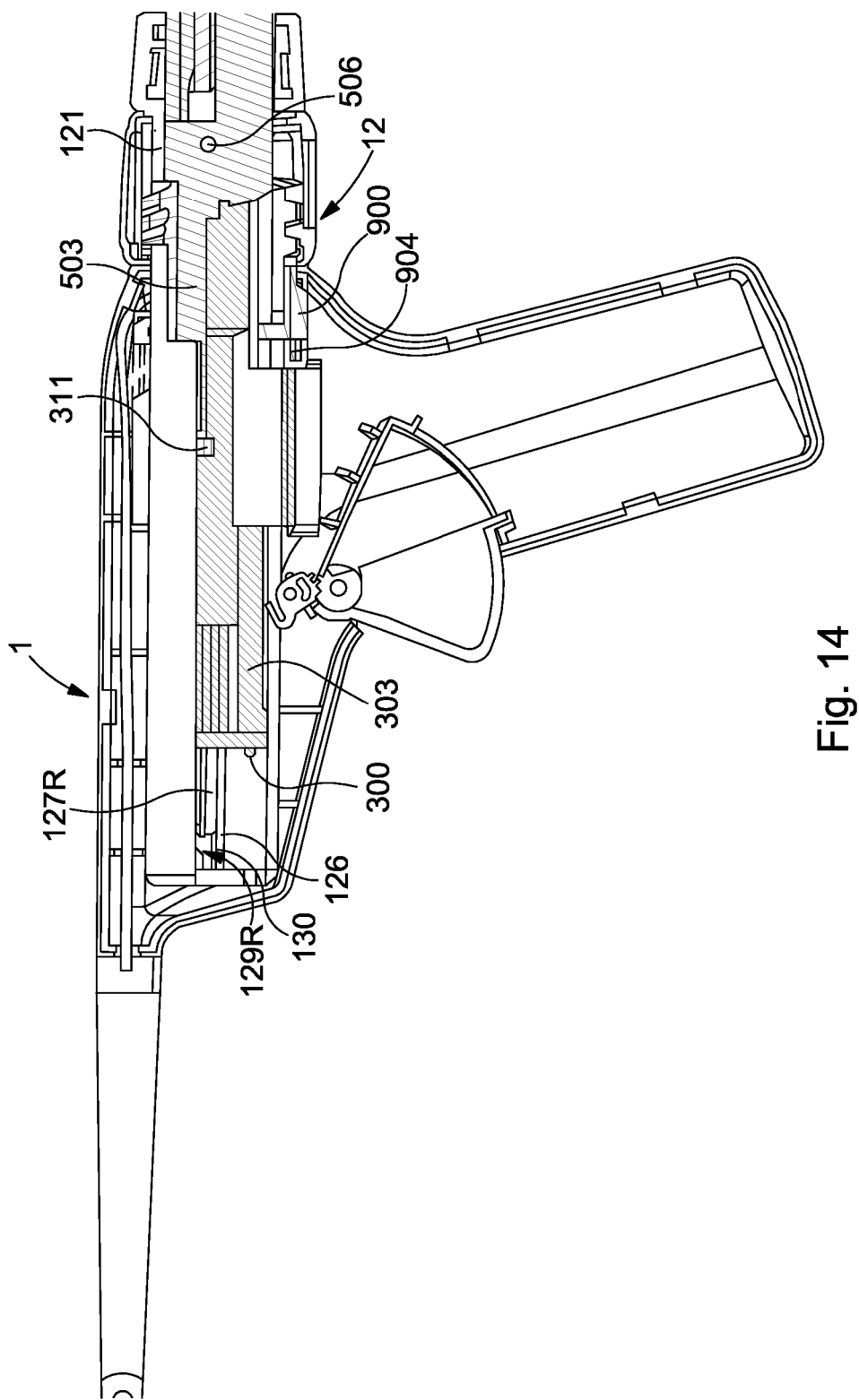
FIG. 14 is similar to FIG. 3, but shows the piston assembly being pushed by the plunger assembly to draw adhesive into the priming chamber.

In the next step of activation, plunger assembly 5 is moved linearly inwardly of the body of the actuator and is guided during this movement by virtue of the pins 506 locating in the linear portion of grooves 124R and 124L (FIGS. 11 and 12). During this linear movement, plunger assembly 5 pushes piston unit 300 to the left (as viewed in FIGS. 3 and 4) so that the piston formed on the end of arm 304 causes adhesive to be drawn through the fine filter 207 into the delivery chamber 202. During this linear movement of plunger assembly 5, priming lock pin 900 remains engaged with priming knob 13 (to prevent rotation thereof). Additionally (and as indicated above) there is no engagement during this stage of either the rotary pawl unit 13 or the pawl 137 with any of the ratchet teeth 307 or 308 on the piston unit 300. More specifically, the piston unit 300 is in an orientation such that its arms 302 and 303 are rotationally displaced from the rotary pawl unit 13 and the pawl 137. Therefore piston unit 300 is free to move from right to left. During this movement, the pins 312 on the base plate 301 of piston unit 300 engage in respective ones of the grooves 127R and 127L, which thereby guide linear movement of the rotary piston unit 300 from right to left. FIG. 14 (which is a view of the applicator 1 with front casing removed) illustrates the internal configuration of the applicator partway through the right to left movement of the piston unit 300. In FIG. 14, the engagement of the ends of one of the arms 503 of the plunger assembly 5 with a contact member 311 can be seen.

The leftwards movement of piston unit 300 continues until the pins 312 reach the ends of transfer runs 127R and 127L of guide unit 126, at which point the pins enter the transition regions 129R and 129L to cause piston unit 300 to effect a rotary movement. Further leftwards and rotary movement of the piston unit 300 is prevented once the pins 301 reach the detent region 130 of the guide unit 126. By this time, plunger assembly 5 has undergone further rotational movement by virtue of the pins 506 to traversing the downstream portion of the grooves 124 which extend around the exterior of neck portion 121 of the applicator. The linear and rotary movement of plunger assembly 5 results, firstly, in the priming lock pin 900 being displaced (against the resilience of living hinge 904). This results in the priming locking pin 900 being disengaged from the priming knob 12 and acting to prevent further rotary and linear motion of plunger assembly 5. Additionally, the rotary position of priming assembly 5 is such that notional projections of its fingers 503 locate between the arms 302 and 303 of the piston unit 300.

Movement of the plunger assembly 5 to the left causes a corresponding movement of sleeve 6 to the left. Air that needs to be expelled during the course of this movement can be exhausted either through the aperture 502a in the knob 502 of plunger assembly 5 (via the aforementioned breather tube) or through the slot 221 (FIG. 7) in the interior wall of the priming chamber 201 (this being allowed by virtue that the flange 605 of fine filter unit 601 effectively rides over the grooves 221). Furthermore, towards the limit of the leftward movement of sleeve 6, the nose 603 thereof engages into recess 210 of fine filter unit 207 to displace the latter to the left from the position shown in FIG. 8 to that shown in FIG. 9 whereby adhesive outlet 204 comes into communication with delivery chamber 202 via adhesive transfer apertures 215 and the annular groove 214. The engagement of the nose 603 (of sleeve 6) into the recess 210 of fine filter unit 207 also seals off communication of adhesive from delivery chamber 202 to priming chamber 201.

Figure 15:
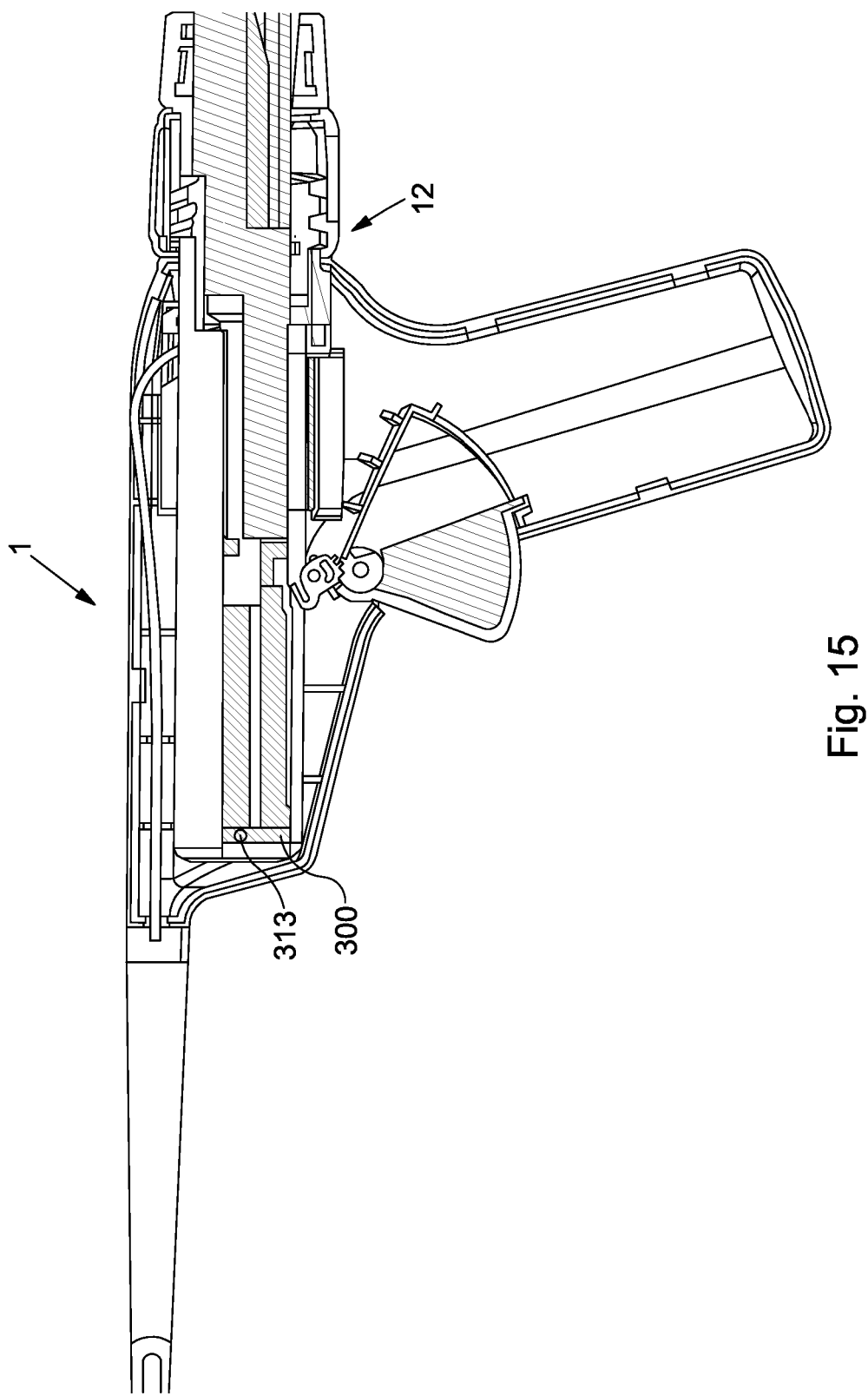
FIG. 15 shows the piston assembly position in which adhesive has been drawn into the priming chamber, with the piston unit being in a position of readiness for movement by the priming carriage to purge the applicator.
Figure 16:
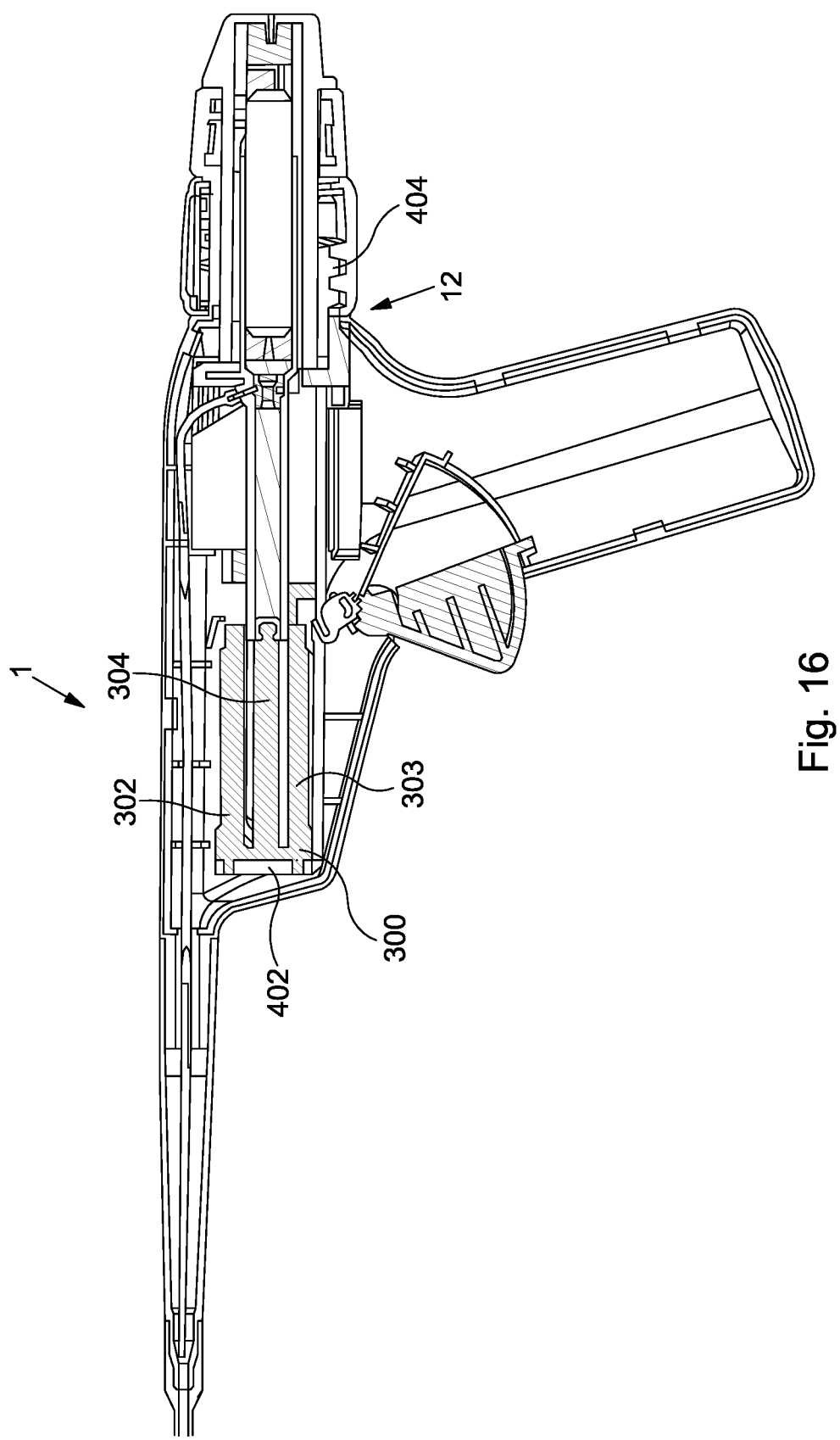
FIG. 16 is a longitudinal sectional view of the applicator in the configuration shown in FIG. 15.

With particular regard to piston unit 300, this now locates (at its left most position) with its pins 313 fitted in the apertures 407 in the base plate 402 of primer carriage 400 (see in particular FIGS. 15 and 16 which illustrate the internal configuration of applicator 1 when piston unit 300 has reached its left most position). This engagement of the pins 313 in apertures 407 prevents further rotational movement of piston unit 3. At the rotational position it has reached, the arms 301 and 302 are positioned such that the pawl 111 will engage one set of ratchet teeth 307 on the piston unit 300 and the pawl 137 when (but only when) the piston unit 300 has been moved a short distance to the right.

In the next step of activation, primer knob 12 is rotated and as a result the part helical screw thread formations 150 on the primer knob 12 interact with the part helical screw thread formations 404 on the primer carriage 402 causing the latter to be moved a short distance to the right. This distance is sufficiently far for two purposes. The first is to move the piston within delivery cylinder 202 a corresponding short distance to the right to cause air and adhesive to be passed via the transfer apertures 215 in fine filter unit 207 into the flexible tube 700. There is sufficient displacement of the piston to expel all air originally present in delivery chamber 202 and also to fill the tube 700 (to the tip of the cannula 8) with adhesive. Secondly, the rightwards movement of piston unit 300 is sufficient such that the pawls 11 and 137 engage a respective set of the ratchet teeth 307 and 308. At this point, each squeeze of the trigger moves the piston unit 300 incrementally to the right to expel a drop of adhesive. During this movement of the piston unit 300, the pins 311 travel along the delivery runs 128 of the guide units 126R. These runs 128 are open at the casing of the applicator and provide the elongate windows 11 referenced in FIG. 1. The position of the pins 311 along the windows 11 is an indication of the degree of travel of the piston unit 300 and therefore an indication of the amount of adhesive remaining in the application. It will be appreciated that movement of the carriage unit 300 to the right during delivery of the adhesive is permitted because the arms 302 and 303 (of piston unit 300) can travel along the grooves 504 between the arms 503 of the plunger assembly 5. It should be appreciated that various modification may be made to the illustrated embodiment of applicator. Thus, for example, a linear mechanism may be used for fracturing the ampule rather than a rotary mechanism. In this case, the plunger assembly may have internal camming surfaces configured such that the plunger assembly may be withdrawn a short distance out of the applicator body to effect fracture of the ampule by virtue of the camming surfaces pressing the wings 219 (associated with delivery chamber 201) progressively towards each other. The camming surfaces may terminate in a step such that rotation of the plunger assembly is required before it can be pushed inwards to allow the priming cylinder to be filled with adhesive in the manner described above.

Alternatively or additionally, alternative types and/or shapes of cannula 8 (e.g. non-linear) may be employed.

The invention claimed is:
1. An applicator for dispensing a liquid, the applicator comprising:
a body,
a holder for holding a supply of liquid to be dispensed,
a nozzle mounted on the body for dispensing the liquid, an elongate priming chamber within the body for receiving the liquid from the holder, an elongate delivery chamber within the body for receiving the liquid from the priming chamber, a piston assembly having a piston located in the delivery chamber and being moveable in a first direction to draw the liquid from the priming chamber into the delivery chamber and in a second opposite direction for passing the liquid from the delivery chamber to the nozzle, a drive arrangement capable of effecting incremental movement of the piston in the second direction for metered dispense of the liquid, and a first actuator for operating the drive arrangement for effecting said incremental movement, wherein the delivery chamber and the priming chamber are coaxial with each other.

2. An applicator as claimed in claim 1 wherein the drive arrangement is configured such that the drive to arrangement is not engaged during initial movement of the piston assembly in the second direction from a limit of the piston assembly's movement in the first direction.

3. An applicator as claimed in claim 1 wherein the piston assembly is moveable in the second direction from an initial fourth position to a fifth position without engagement of the drive arrangement and is moveable from the fifth position to a sixth position by operation of the drive arrangement.

4. An applicator as claimed in claim 3 comprising a carriage engageable by the piston assembly when at the fourth position and being operable to effect movement of the piston assembly in the second direction from the fourth to the fifth position.

5. An applicator as claimed in claim 4 wherein a second actuator is rotably mounted on the body of the applicator, said second actuator having a screw thread formation operatively associated with a complementary screw thread formation provided on the carriage, whereby rotation of the second actuator effects movement of the carriage in the second direction to move the piston assembly from the fourth to fifth position.

6. An applicator as claimed in claim 1 wherein the applicator is configured such that the holder is linearly moveable in the first direction and adapted, during the linear movement, to engage the piston assembly and effect movement thereof in the first direction and subsequently rotationally moveable towards a limit of the holder's movement in the first direction to disengage the holder from the piston assembly to permit movement thereof in the second direction.

7. An applicator as claimed in claim 1 wherein the holder holds an elongate frangible ampoule of the liquid to be dispensed, the holder being associated with a mechanism for fracturing the ampoule.

8. An applicator as claimed in claim 7 wherein the ampoule is coaxial with the piston.

9. An applicator as claimed in claim 7 wherein the ampoule is held in a sleeve and said sleeve is provided with a filter element at a sleeve end adjacent to the piston assembly.

10. An applicator as claimed in claim 7 wherein the holder is rotatable to fracture the ampoule.

11. An applicator as claimed in claim 10 wherein the holder has camming surfaces effective, on rotation of the holder, to fracture the ampoule.

12. An applicator as claimed in claim 6 wherein the holder is linearly moveable to fracture the ampoule.

13. An applicator as claimed in claim 1 wherein the liquid is a curable cyanoacrylate composition.

14. An applicator for dispensing a liquid, the applicator comprising:

a body, a holder for holding a supply of liquid to be dispensed, a nozzle mounted on the body for dispensing the liquid, an elongate priming chamber within the body for receiving the liquid from the holder, an elongate delivery chamber within the body for receiving the liquid from the priming chamber, a piston assembly having a piston located in the delivery chamber and being moveable in a first direction to draw the liquid from the priming chamber into the delivery chamber and in a second opposite direction for passing the liquid from the delivery chamber to the nozzle, a drive arrangement capable of effecting incremental movement of the piston in the second direction for metered dispense of the liquid, and a first actuator for operating the drive arrangement for effecting said incremental movement, wherein during movement of the piston assembly in the first direction the drive arrangement is disengaged from the piston assembly.

15. An applicator as claimed in claim 14 wherein the piston assembly is linearly moveable in the first direction from a first position to a second position and is then rotationally moveable from the second position to a third position to allow for movement of the piston assembly in the second direction by operation of the drive arrangement.

16. An applicator as claimed in claim 15 wherein the piston assembly has an arm extending externally of the delivery chamber parallel to the second direction and the drive arrangement comprises a set of rack teeth provided on the arm, and a drive element operable by the first actuator and capable of engaging the rack teeth to effect movement of the piston assembly in the second direction.

17. An applicator as claimed in claim 14 wherein the priming chamber and the delivery chamber are coaxial.

18. An applicator as claimed in claim 17 comprising an intermediate chamber between adjacent ends of the priming and delivery chambers and coaxial therewith, a liquid outlet connected to the intermediate chamber, and an axially moveable filter in the intermediate chamber, said axially moveable filter being configured as a valve and being moveable from a first position in which the liquid outlet is closed to liquid flow from the delivery chamber but the valve allows the liquid to pass from the priming chamber to the delivery chamber, to a second position in which the liquid can flow from the delivery chamber to the outlet but not between the priming chamber and delivery chamber.

19. An applicator as claimed in claim 14 wherein the drive arrangement is configured such that the drive to arrangement is not engaged during initial movement of the piston assembly in the second direction from a limit of the piston assembly's movement in the first direction.

20. An applicator as claimed in claim 14 wherein the piston assembly is moveable in the second direction from an initial fourth position to a fifth position without engagement of the drive arrangement and is moveable from the fifth position to a sixth position by operation of the drive arrangement.

21. An applicator as claimed in claim 14 wherein the applicator is configured such that the holder is linearly moveable in the first direction and adapted, during the linear movement, to engage the piston assembly and effect movement thereof in the first direction and subsequently rotationally moveable towards a limit of the holder's movement in the first direction to disengage the holder from the piston assembly to permit movement thereof in the second direction.

22. An applicator as claimed in claim 14 wherein the holder holds an elongate frangible ampoule of the liquid to be dispensed, the holder being associated with a mechanism for fracturing the ampoule.

23. An applicator as claimed in claim 14 wherein the liquid is a curable cyanoacrylate composition.

* * * * *